United States Patent
Kolb et al.

(10) Patent No.: US 10,035,016 B2
(45) Date of Patent: *Jul. 31, 2018

(54) ELECTRICAL STIMULATION DEVICE

(71) Applicant: ELIDAH, Inc., Monroe, CT (US)

(72) Inventors: Gloria Kolb, Sandy Hook, CT (US); Eric Kolb, Sandy Hook, CT (US)

(73) Assignee: ELIDAH, Inc., Monroe, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/456,920

(22) Filed: Mar. 13, 2017

(65) Prior Publication Data
US 2017/0182320 A1    Jun. 29, 2017

Related U.S. Application Data

(63) Continuation-in-part of application No. 14/678,058, filed on Apr. 3, 2015, now Pat. No. 9,623,231.

(60) Provisional application No. 61/979,065, filed on Apr. 14, 2014, provisional application No. 62/404,329, filed on Oct. 5, 2016.

(51) Int. Cl.
*A61N 1/36* (2006.01)
*A61N 1/04* (2006.01)

(52) U.S. Cl.
CPC ....... *A61N 1/36007* (2013.01); *A61N 1/0452* (2013.01); *A61N 1/0476* (2013.01); *A61N 1/0492* (2013.01); *A61N 1/36014* (2013.01)

(58) Field of Classification Search
CPC ............ A61N 1/036007; A61N 1/0475; A61N 1/0492; A61N 1/36014
See application file for complete search history.

(56) References Cited

U.S. PATENT DOCUMENTS

| | | | |
|---|---|---|---|
| 4,635,641 A | 1/1987 | Hoffman | |
| 4,742,833 A | 5/1988 | Barsom | |
| 5,562,717 A | 10/1996 | Tippey et al. | |
| 5,871,534 A | 2/1999 | Messick et al. | |

(Continued)

FOREIGN PATENT DOCUMENTS

WO    2012/116407 A1    9/2012

OTHER PUBLICATIONS

Non-Invasive Urinary Incontinence Treatment—INNOVO® Product; retrieved from https://www.restorethefloor.com/.

(Continued)

*Primary Examiner* — Paula J Stice
(74) *Attorney, Agent, or Firm* — Alix, Yale & Ristas, LLP

(57) ABSTRACT

A skin surface electrical stimulation device or electrode for use in the treatment of various conditions. The electrode has a plurality of conductive regions spaced from one another in predetermined positions around a non-conductive body that extends longitudinally from a head portion to a tail portion. At least two posterior conductors are positioned in the tail portion and spaced laterally from each other. One or more anterior conductors are positioned in the head portion and spaced longitudinally from the respective posterior conductors. An opening extends longitudinally rearwardly from an intermediate position in the body to split the tail portion into right and left portions. The electrode device is configured for placement proximate perineal area in an individual or animal for delivery of treatment via generating an electrical charge through respective conductors.

25 Claims, 39 Drawing Sheets

(56) References Cited

U.S. PATENT DOCUMENTS

| | | | |
|---|---|---|---|
| 6,324,432 B1* | 11/2001 | Rigaux | A61N 1/0452 |
| | | | 600/372 |
| 6,553,266 B1 | 4/2003 | Yuang | |
| 6,756,521 B1 | 6/2004 | Breitkopf | |
| 7,280,873 B2 | 10/2007 | Freed et al. | |
| 7,855,653 B2 | 12/2010 | Rondoni et al. | |
| 7,925,323 B2 | 4/2011 | Meyer | |
| 8,634,920 B2 | 1/2014 | Hagege | |
| 8,738,112 B2 | 5/2014 | Choe et al. | |
| 2005/0154438 A1 | 7/2005 | Fuller et al. | |
| 2008/0215128 A1 | 9/2008 | Rainey et al. | |
| 2010/0318018 A1 | 12/2010 | Schonenberger et al. | |
| 2011/0276108 A1 | 11/2011 | Crowe et al. | |
| 2013/0023816 A1 | 1/2013 | Bachinski et al. | |
| 2013/0327342 A1 | 12/2013 | Watschke et al. | |
| 2014/0005752 A1 | 1/2014 | Hershey | |
| 2014/0155954 A1* | 6/2014 | Lee | A61N 1/36014 |
| | | | 607/48 |

OTHER PUBLICATIONS

International Search Report and Written Opinion dated Oct. 25, 2017 for International Patent Application No. PCT/US2017/055279.

Supplementary European Search Report dated Nov. 6, 2017 for European Patent Application No. 15779494.2.

* cited by examiner

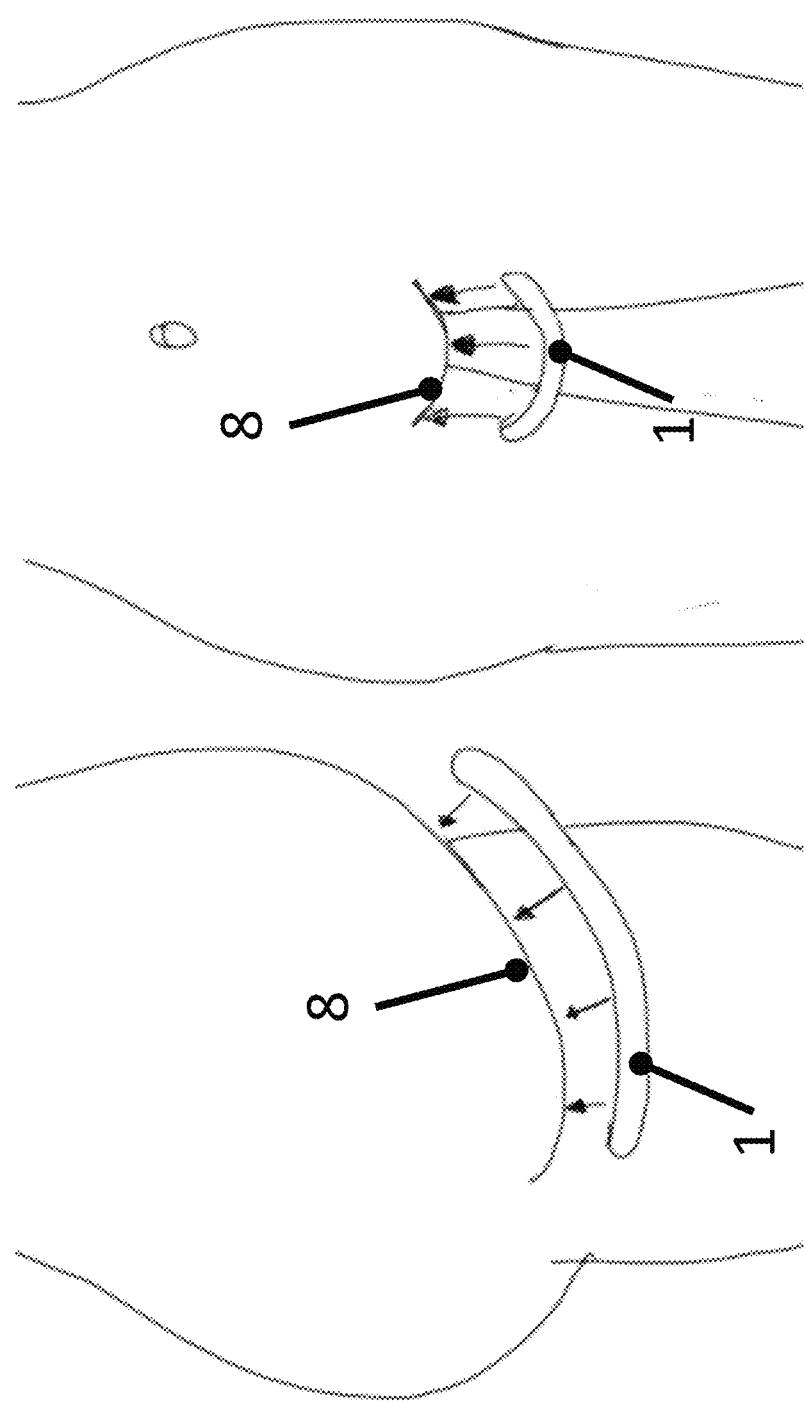

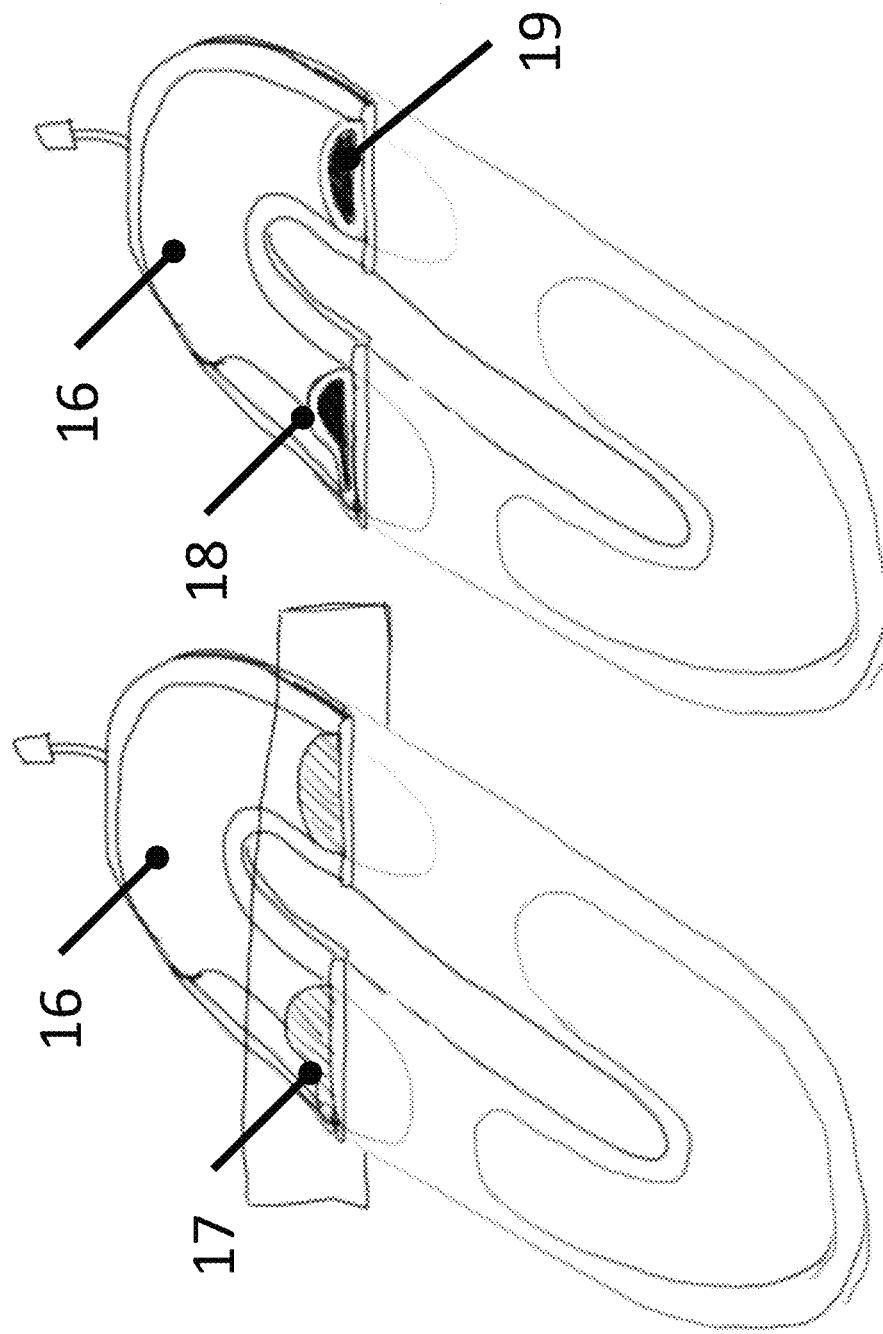

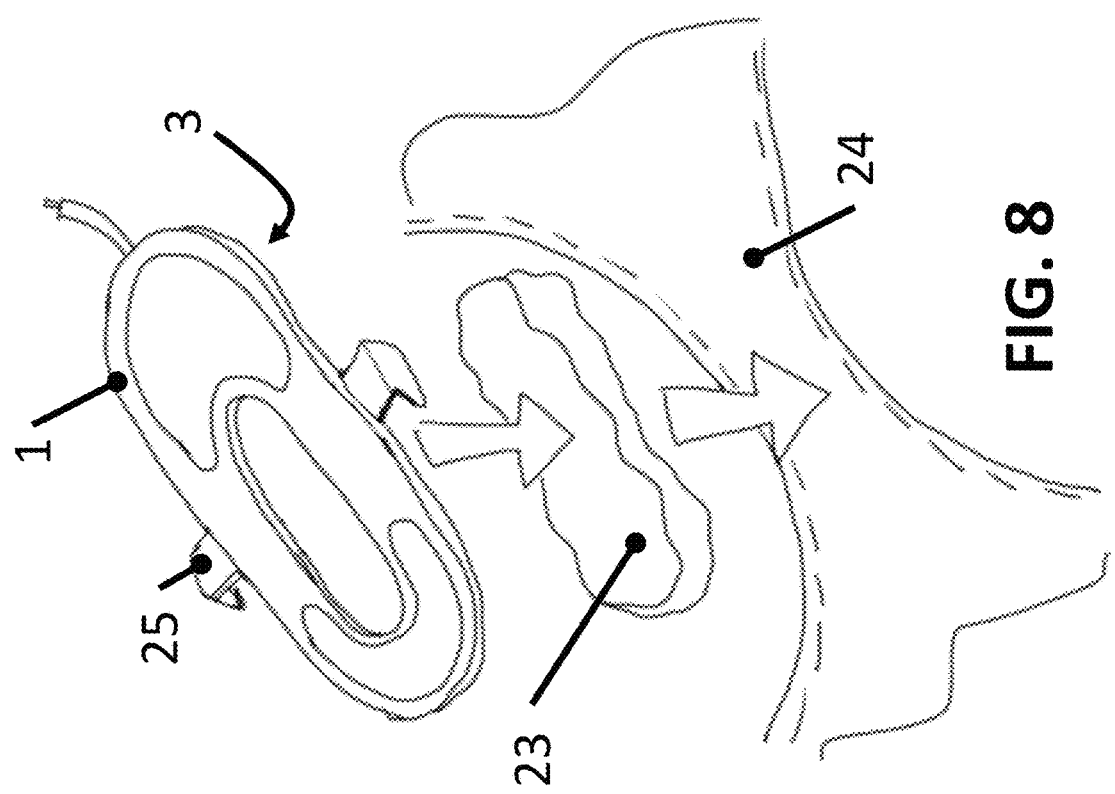

ELECTRICAL STIMULATION DEVICE

CROSS-REFERENCE TO RELATED APPLICATION

This application is a continuation-in-part of U.S. patent application Ser. No. 14/678,058, now U.S. Pat. No. 9,623,231, filed Apr. 3, 2015, which claims priority to U.S. Provisional Patent Application No. 61/979,065, for Device to Treat Incontinence, filed Apr. 14, 2014, and claims priority to U.S. Provisional Patent Application No. 62/404,329, filed Oct. 5, 2016, the entire disclosures of which is hereby incorporated by reference.

BACKGROUND OF INVENTION

The disclosure relates to an electrical stimulation device for treatment of an individual or animal, for example via transcutaneous electrical muscle stimulation. Conditions that are treatable with the disclosed electrical stimulation device include, without limitation, stress incontinence, urge incontinence, mixed incontinence, male urinary incontinence, pelvic prolapse, vulvodynia, complications following prostate removal and fecal incontinence. Aspects described herein serve to drive improved patient compliance relative to known treatments.

Electric muscle stimulation (EMS) and transcutaneous electrical nerve stimulation (TENS) have proven effective tools for toning and retraining muscles as well as calming or stimulating nerves. Important to its efficacy is the ability to stimulate the specific muscles and/or reach certain nerves, and this is complicated when the targeted muscles are deep within the patient's tissue. Several factors impact the ability of the delivered electric current to stimulate deep tissue muscles including the shape and frequency of the pulse waveform, the electrode size and configuration, positioning of the electrodes, and the continuity of the electrode-skin interface.

Urinary incontinence, as an exemplary condition, affects as many as one third of woman over the age of 30. One cause is a weakening of pelvic floor muscles. Clinical studies have shown EMS and/or TENS to be effective at resolving the symptoms of incontinence; however, two thirds of women who suffer from incontinence forgo medical treatment. Their failure to adopt or comply with EMS or TENS treatment regimens is at least partly due to the manner in which the stimulation is provided. One known method is through surgical implantation of a sacral nerve stimulator. Such implantable devices are relatively permanent and pose inherent risks including infection. EMS and/or TENS treatment is also commonly provided via an intravaginal probe. Many women have psychological and physiological challenges accepting this form of treatment. Further, its configuration necessitates usage in a private location, limiting many patients' ability to obtain treatment multiple times per day. Thirdly, conventional EMS electrode pads can be applied to the perineal tissues of the patient in patterns aimed at stimulating the pelvic floor muscles. This commonly requires four electrode pads and placement by a trained clinician. As with the other stimulation devices, these surface electrodes have proven effective, but they are difficult for an individual to apply to herself, are difficult to maintain in contact for an extended period of time, are difficult to administer multiple times per day, fail to accommodate leakage, and do not allow discreet use.

Thus a need exists for a device to deliver EMS treatment to the pelvic floor that is easy to apply, can be worn for an extended period of time, allows multiple convenient treatments per day, can accommodate leakage and be worn discreetly by the user.

SUMMARY OF INVENTION

In one embodiment an electrical stimulation device includes a body made from an electrically insulating material having a head portion transitioning longitudinally to a tail portion. At least one activatable anterior conductor is positioned on the head portion and at least two activatable posterior conductors are positioned on the tail portion. The body has a lateral width defined between a left edge and a right edge extending the longitudinal length from the head portion to the tail portion with the lateral width at an intermediate portion being smaller than the lateral width of the tail portion. A longitudinally extending void space is positioned within the body laterally between the left and right edges and longitudinally between the head portion and tail portion. The void space splits the tail portion into a left side and a right side. The at least one anterior conductor and at least two posterior conductors cooperate to pass an electrical charge between one another to treat an area on the individual or animal on which the conductors are placed in contact.

In another embodiment, an electrical stimulation device has a body with a contact side and a non-contact side. The body extends longitudinally between an anterior end and posterior end and laterally between a left edge and right edge with a sagittal plane extending longitudinally between the left and right edges. At least one activatable conductor is positioned proximate the anterior end on the contact side of the body. At least two posterior conductors are positioned proximate the posterior end of the contact side of the body. At least one of the at least two posterior conductors is positioned on each side of the sagittal plane. A spacing extending in the body in a direction toward the posterior end from an intermediate position located between the anterior end and posterior end thereby splitting a portion of the body into a left side and right side. At least one posterior conductor is positioned on each of the left side and the right side with a portion of the spacing disposed therebetween. The contact side defines a surface configured for interfacing with the perineal region in an individual or animal whereby electrical current generated through the conductors when activated penetrates into the perineal region.

BRIEF DESCRIPTION OF DRAWINGS

Aspects of the preferred embodiments will be described in reference to the drawings, wherein like reference numerals reflect like elements throughout:

FIG. 4 is a lateral and anterior view depicting placement of an electrode embodiment.

FIG. 5a is a section view of an electrode embodiment.

FIG. 5b is a section view of an electrode embodiment.

FIG. 8 is an exploded perspective view of an electrode embodiment.

DETAILED DESCRIPTION OF A PREFERRED EMBODIMENTS

Among the benefits and improvements disclosed herein, other objects and advantages of the disclosed embodiments will become apparent from the following wherein like numerals represent like parts throughout the several figures. Detailed embodiments of an electrical stimulation device for use with patients are disclosed; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "In some embodiments" and "in some embodiments" as used herein do not necessarily refer to the same embodiment(s), though it may. The phrases "in another embodiment" and "in some other embodiments" as used herein do not necessarily refer to a different embodiment, although it may. Thus, as described below, various embodiments may be readily combined, without departing from the scope or spirit of the invention. Moreover, various elements from different depictions of embodiments may be combined into a single embodiment of the device.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on.

Further, the terms "substantial," "substantially," "similar," "similarly," "analogous," "analogously," "approximate," "approximately," and any combination thereof mean that differences between compared features or characteristics is less than 25% of the respective values/magnitudes in which the compared features or characteristics are measured and/or defined.

Many of the disclosed embodiments facilitate pelvic floor muscle contraction through electrical muscle stimulation delivered through the perineal tissues. For the purpose of this disclosure the term pelvic floor muscles refers to all musculature and associated nerves that act in maintaining continence. Further, for purpose of this disclosure the term perineal tissue(s) is intended to include the broad area of superficial tissue in the region of the perineum. Embodiments of the device are used to effectively treat stress, urge, mixed or other urinary incontinence in male or female subjects, pelvic prolapse, vulvodynia, fecal incontinence and complications following prostate removal.

Figure 1:
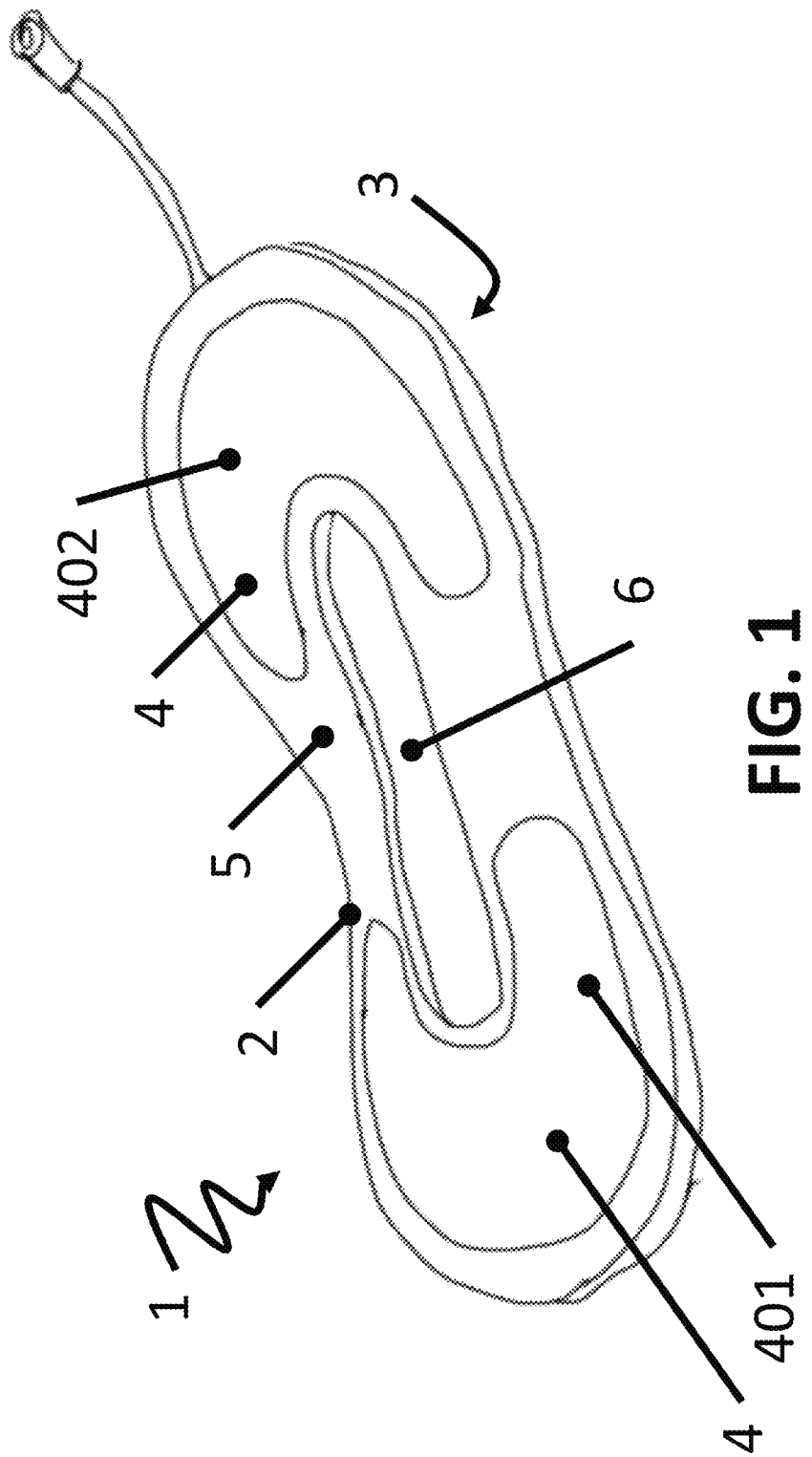
FIG. 1 is a perspective view of an electrode embodiment according to the disclosure.
Figure 2:
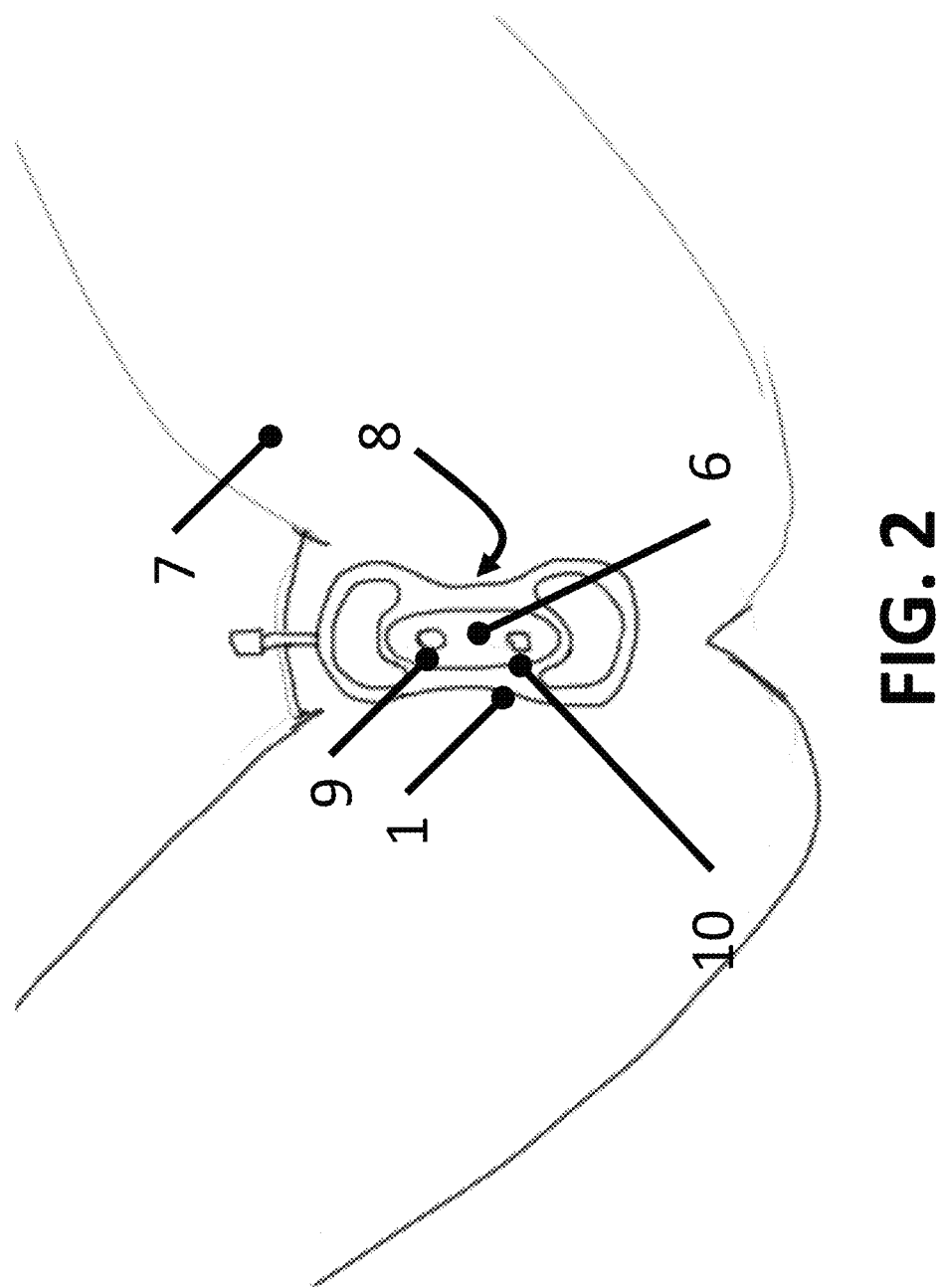
FIG. 2 is a view depicting an electrode embodiment positioned over the perineal tissue.

Referring to FIG. 1, the subject electrode or electrical stimulation device 1 is depicted with a body comprising a skin contacting side or surface 2 and an outward facing non-contact side or surface 3. The skin contacting surface 2 includes one or more conductive regions 4 and one or more non-conductive (i.e. insulated) regions 5. The outward facing surface 3 is substantially electrically insulated from the conductive regions 4. Further, the electrode 1 includes void space defining an egress 6 at an intermediate position, and preferentially along its midline. Referring to FIG. 2, when the electrode 1 is positioned against the skin 7 and over the perineal tissue 8 such that the egress 6 is centered over the external urethral opening 9, vagina 10 and/or anus, the egress 6 allows bodily fluid to flow past the electrode 1 without substantially interrupting contact between the skin contacting surface 2 and the skin 7.

In one embodiment a first conductive region 401 serves as an anode and a second conductive region 402 serves as a cathode. When connected to an EMS device current flows from the anode, through the user's tissue and into the cathode. In this embodiment the conductive regions of the electrode are electrically isolated from one another and spaced sufficiently to allow the electrical current to penetrate to the depth of the pelvic floor muscles.

Figure 3:
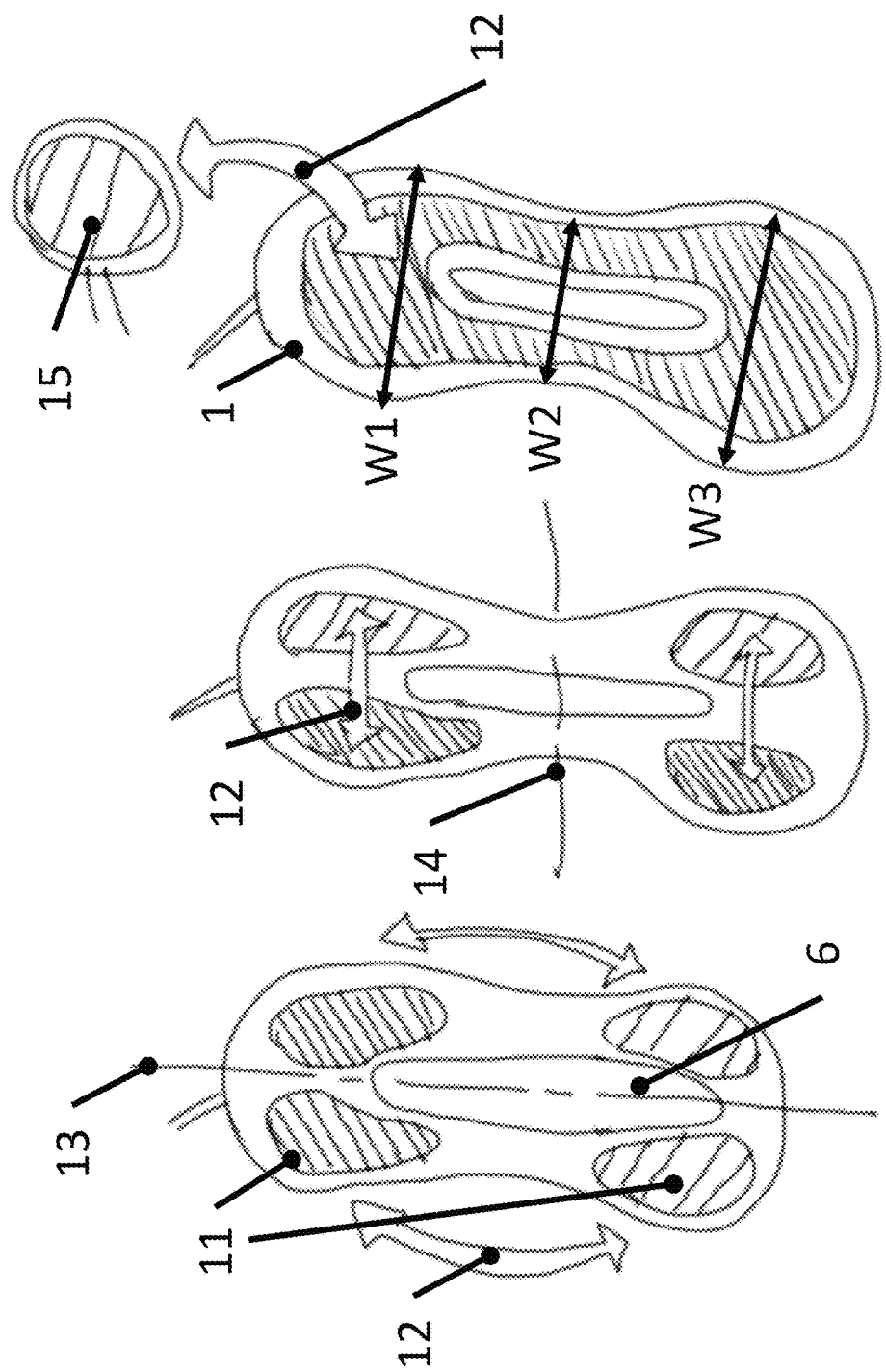
FIG. 3 is a view depicting several alternate embodiments of the disclosed electrode.

Referring to FIG. 3, in one embodiment an anode-cathode pair 11 is located laterally on each side of the egress 6 such that current 12 flows along a sagittal plane 13. In another embodiment an anode is located on one lateral side of the electrode and the corresponding cathode is located on the opposing lateral side such that current 12 flows along a coronal plane 14. In yet another embodiment the subject perineal tissue contacting electrode 1 includes an anode but no corresponding cathode. For this embodiment a separate conventional electrode 15 placed elsewhere on the patient serves as the cathode.

The shape of the perineal tissue varies from patient to patient and also changes with changing body position, for example moving from a seated to standing position. However, conventional electrodes are substantially flat and circular or rectangular in shape. Given the contoured shape of the perineal tissue such conventional electrodes are not well suited for maintaining electrode-skin contact. Still referring to FIG. 3, the embodiment of the electrode 1 has a generally hourglass shape (i.e. profile) with an outer edge periphery that tapers inward toward a longitudinal intermediate portion, generally defining three lateral widths (W1, W2, W3), wherein W2 is located between and is less than W1 and W3. Referring to FIG. 4, in one embodiment the subject electrode 1 is contoured to fit the perineal tissue 8. For example, the skin contacting surface of the electrode may have a predefined curvature to accommodate anatomic curvature in the sagittal plane. Similarly, the skin contacting surface may be concave in the coronal plane to accommodate labial tissue.

Referring to FIG. 5a, in one embodiment the conductive region 16 is composed of a compliant conductive polymer 17 that is locally compressible to accommodate the user's anatomy. In one embodiment this conductive polymer has a local thickness of greater than 2 mm. In another embodiment (FIG. 5b) the conductive region comprises a conductive pouch 18 filled with a conductive liquid, gel or foam 19. The filled pouch construct permits local deformation of the conductive region to accommodate varied user anatomy. Similarly, non-conductive regions of the electrode may also comprise a filled pouch construct to permit local deformation and conformity with user anatomy. Maintaining the electrode-tissue contact in the non-conductive region is beneficial in that it typically inhibits fluid from accumulating along the skin. An additional advantage of the conductive fluid, gel or foam 19 filled pouch configuration is that the user can place the electrode in a refrigerator freezer prior to use. The cooled electrode may then act as a cold compress for local treatment of pain in nerves during treatment.

Figure 7:
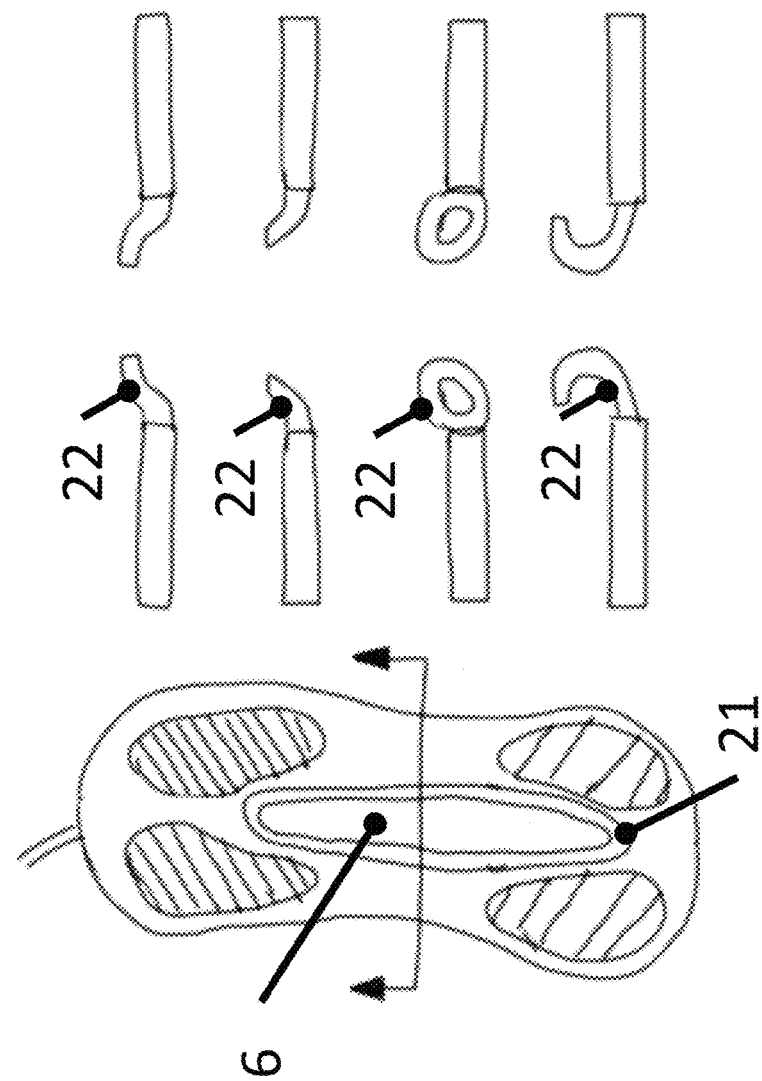
FIG. 7 is a section view of several alternate electrode embodiments, showing different geometries of the egress.
Figure 6:
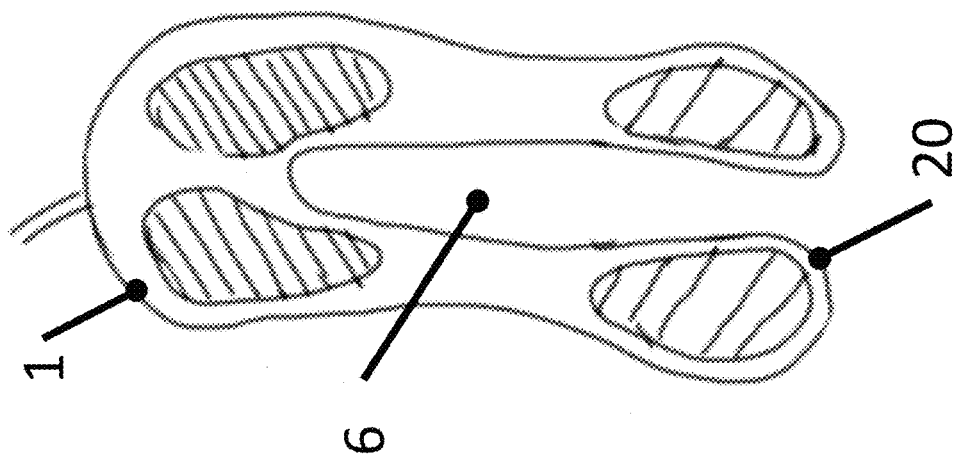
FIG. 6 shows another embodiment of the disclosed electrode.

The egress can have various peripheral shapes, including circular, ovular, triangular, rectangular, or combinations thereof. Referring to FIG. 6, in one embodiment the egress 6 extends longitudinally through the posterior edge 20 of the electrode 1. Referring to FIG. 7, in another embodiment the periphery 21 of the egress 6 has geometry and material compliance sufficient to act as a gasket 22 and resist flow of bodily fluid along the electrode-skin interface. Various gasket geometries are depicted in the cross-sectional views in FIG. 7.

In another embodiment the non-conductive region is comprised of a material and structure that wicks moisture away from the skin-electrode interface. For example, the non-conductive region could be constructed of a wicking fabric or an absorbent hydrogel.

Referring to FIG. 8, in one embodiment the outward facing surface 3 (i.e. non-skin contacting surface) of the electrode 1 includes an attachment portion enabling the user to temporarily affix the electrode to an underlying absorbent pad 23 or undergarment 24. Exemplary features include adhesives, plastically deformable tabs 25 and hook and loop fasteners.

Figure 9:
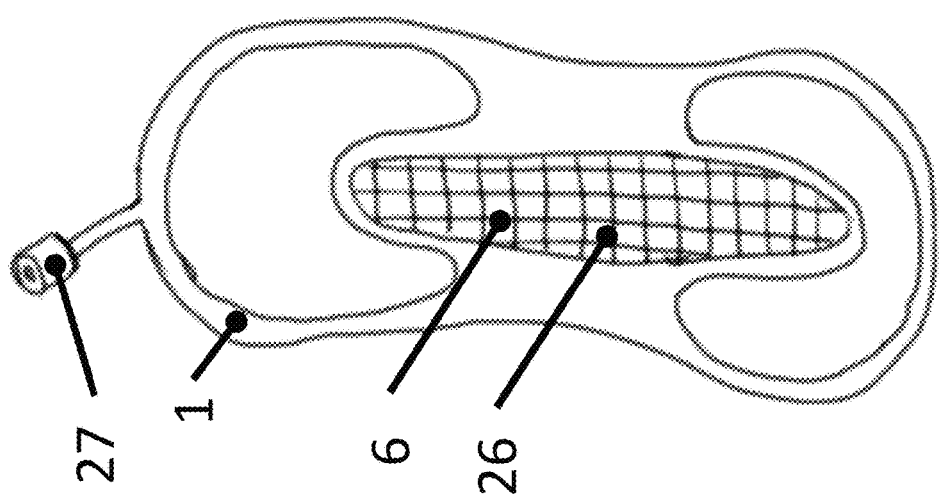
FIG. 9 is a view of an electrode embodiment.

Referring to FIG. 9, in certain embodiments the egress 6 through which bodily fluids pass is completely open. In other embodiments that space is occupied by a permeable structure through which the bodily fluids may pass, for example an open mesh 26. The mesh provides a degree a structure to the electrode 1 to maintain its shape and aide in placement. In another embodiment the back surface of the permeable structure comprises an adhesive to aide in temporarily affixing the electrode to an underlying absorbent pad 23 or undergarment 24.

Figure 10:
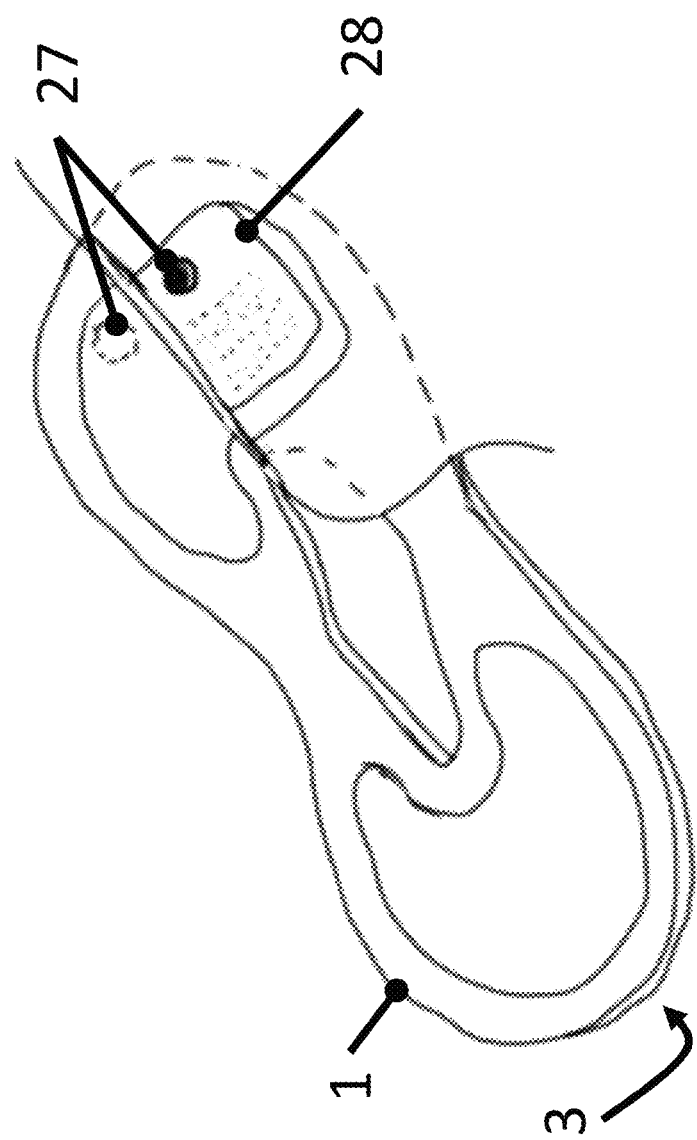
FIG. 10 is a cutaway perspective view of an electrode embodiment.

The electrode comprises one or more connectors 27 for connecting the electrode to a control unit (or pulse generator). Exemplary connectors include pins and snaps. Further, the electrode comprises conductive elements that permit current flow from the connector to the conductive region(s). With embodiments that include an anode and cathode within a single electrode, the conductive elements are insulated from one another within the electrode. These conductive elements may be wires or other conductive media including carbon or silver films. In certain embodiments the connectors 27 are provided at the end of wire leads with a length sufficient to reach the EMS device. In other embodiments the connectors 27 are located directly on the skin contacting surface 2 or outward facing surface 3 of the electrode 1. Referring to FIG. 10, in one embodiment the connectors 27 allow the EMS device 28 to be secured against the outward facing surface in the vicinity of the perineal tissues. In one embodiment the wire leads leading to anode and cathode form a single cable with one or more connector to the EMS device.

Figure 11:
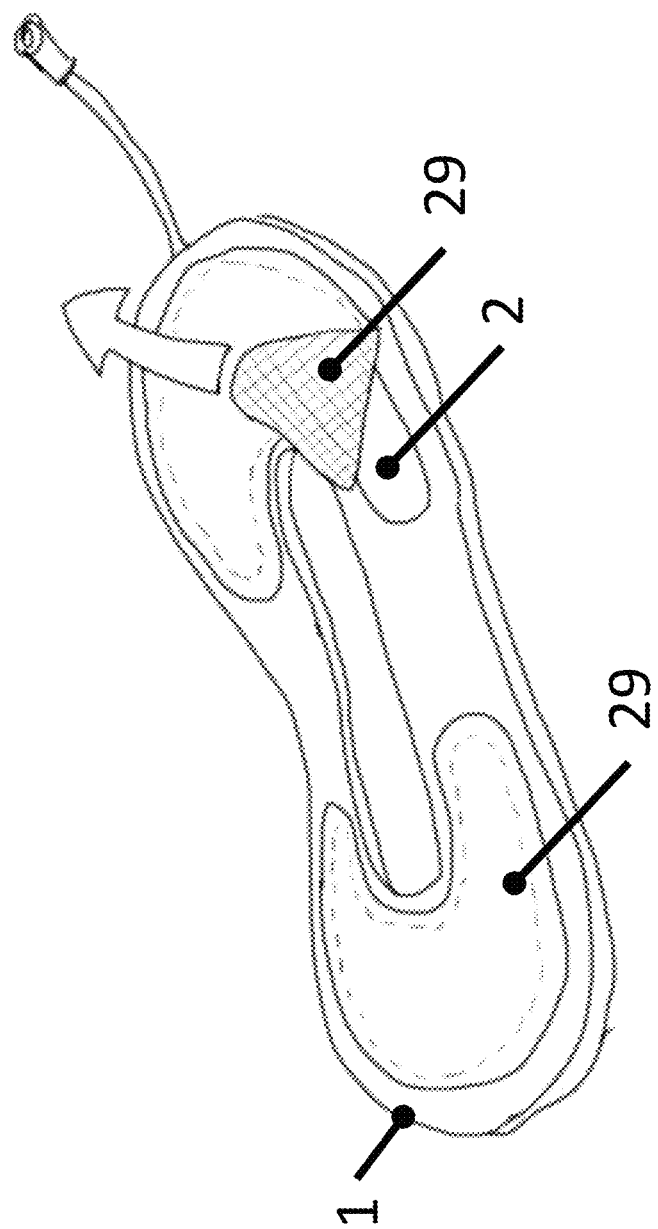
FIG. 11 is a perspective view of an electrode embodiment.

The electrode may be configured as either a disposable device or a reusable device. With the disposable configuration the user would wear the electrode for one day or several days and then discard it and use another electrode thereafter. With the reusable device configuration the user would clean the electrode between uses and use it for an extended period of time, for example, more than 1 week. Referring to FIG. 11, to facilitate cleaning of the reusable electrode 1, one embodiment includes an electrically conductive thin film cover 29 component that is placed on the skin contacting surface 2 and replaced between uses. This thin film cover 29 may include one or more adhesive sides to facilitate positioning relative to the electrode and contact with the skin. In one embodiment the thin film could be a hydrogel. To enhance reusability portions of the device may be comprised of silicone or similar durable and pliable polymer. The outward facing non-contact surface 3 may be substantially non-electrically conductive polymer. The skin contacting surface 2 may be comprised of both electrically conductive and non-conductive polymers. The electrode may be fabricated through multiple molding operations. These multiple molding operations may include over-molding portions of the electrode over wires.

Figure 12:
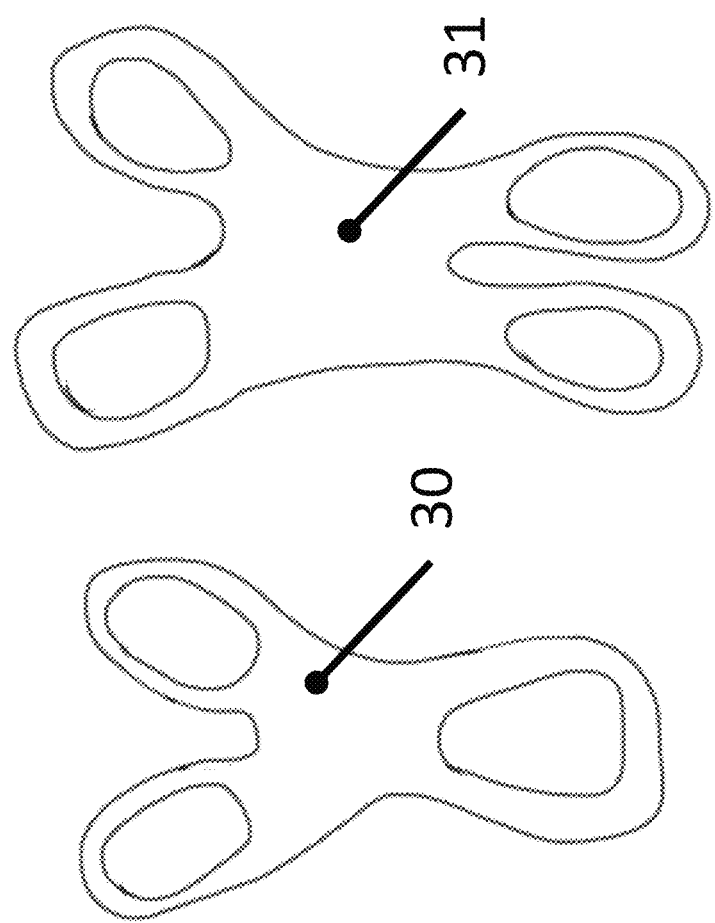
FIG. 12 shows two electrode embodiments of varying configurations.

Several of the aforementioned embodiments are best suited for use on female anatomy. Referring to FIG. 12, additional embodiments that accommodate male anatomy take the form of a "Y" 30 or "X" 31, and although an egress is not present, many of the aforementioned features that maintain prolonged contact between the electrode and skin are present. Further, the "Y" 30 shaped electrode can be configured such that the stem portion of the "Y" extends posteriorly toward the low back and positioning at least one conductive region 4 to stimulate the pudendal nerve.

Figure 13:
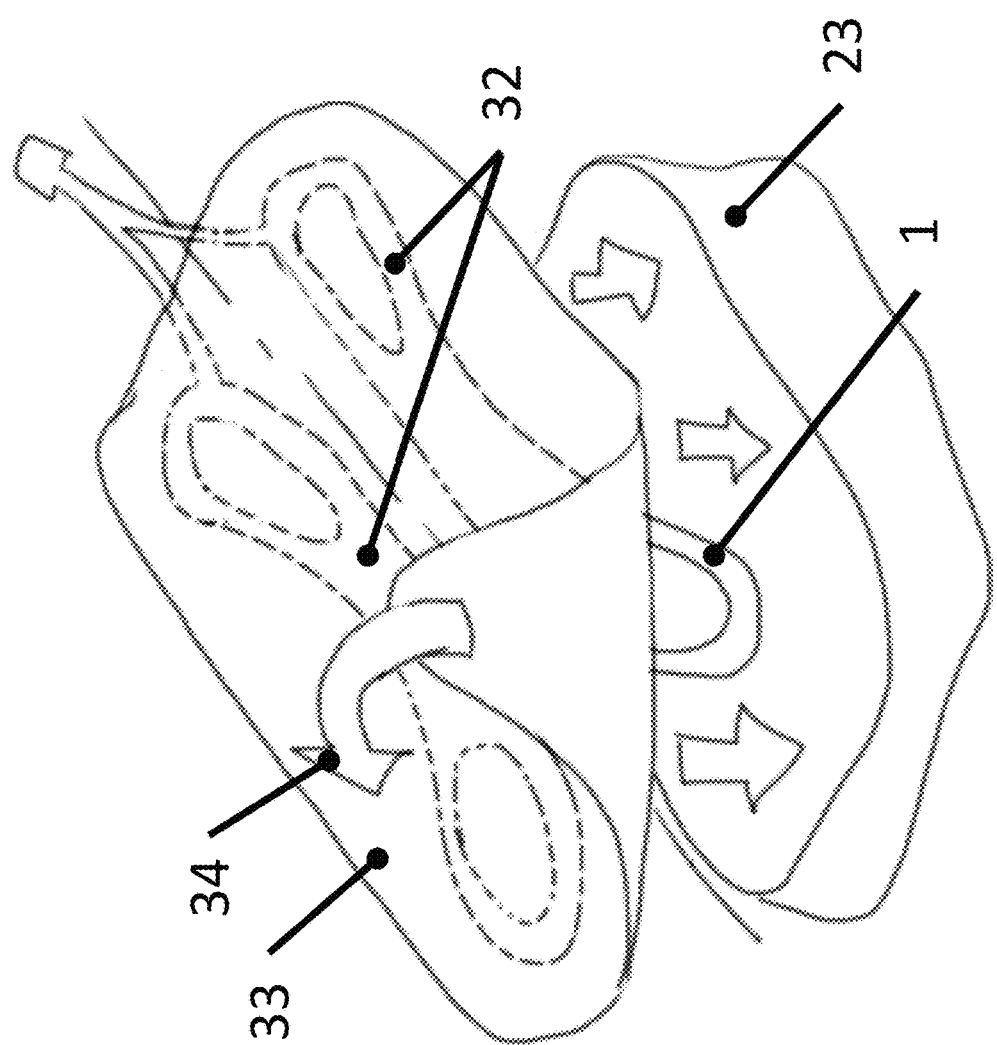
FIG. 13 is an exploded perspective view of an electrode embodiment.

Similarly, the device may comprise a pair of electrodes that mirror one another and are shaped to fit the perineal tissue with a space in between that would allow egress of bodily fluids. Referring to FIG. 13, in one embodiment this electrode pair 32 is removably connected to a transfer sheet 33. The transfer sheet 33 maintains the relative position of the individual electrodes 1 during electrode positioning and is subsequently removed 34. In another embodiment each electrode 1 in the electrode pair 32 adheres to an absorbent pad 23 or undergarment.

In another embodiment electrode 1 is removably connected to transfer sheet 33. Here, transfer sheet 33 facilitates handling and positioning of the device by the user. One method of applying the device includes steps of (1) partially peeling the transfer sheet 33 away from the electrode, (2) positioning the exposed portion of the electrode 1 against the skin, (3) fully peeling the transfer sheet 33 away from the electrode 1 and (4) securing the entirety of the electrode 1 against the skin. The transfer sheet 33 may have a shape and surface area substantially larger than the electrode 1 (shown) or have a shape and surface area substantially similar to the electrode 1. The transfer sheet 33 may comprise a handling tab that facilitates positioning and separation from the electrode 1. The transfer sheet 33 may include markings that facilitate positioning of the electrode 1 by providing anatomical references. The transfer sheet 33 may additionally provide a means for maintaining hydration and/or tack of the skin contacting surface 2.

Throughout this disclosure, use of the term perineal tissue is not meant to limit application of this invention to a precise area. For example, with certain embodiments a portion of the electrode may extend anterior, posterior or laterally to the perineum, with a goal of positioning the conductive regions at anatomic sites best suited for transmitting current to the pelvic floor.

Figure 14:
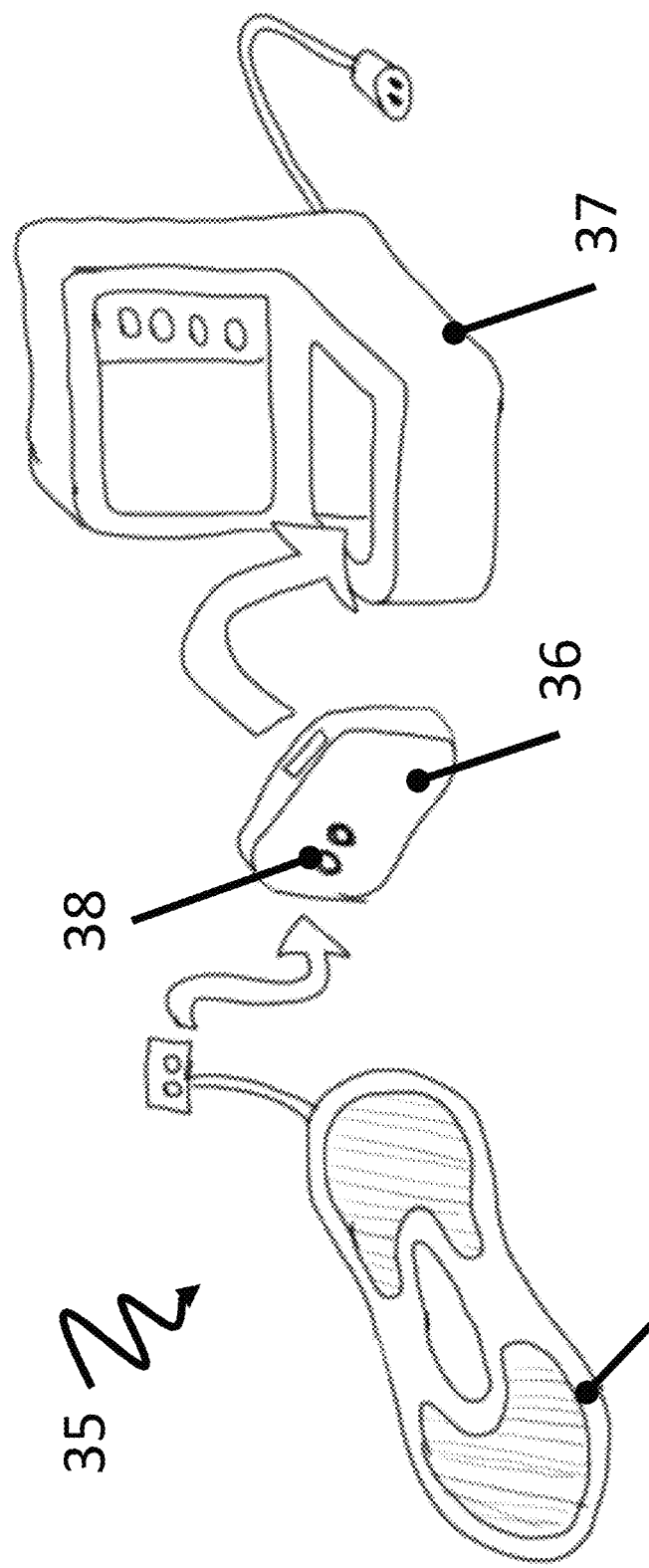
FIG. 14 is a perspective view of an incontinence treatment system.

Referring to FIG. 14, another embodiment of the invention is an incontinence treatment system 35 comprising the aforementioned electrode 1 and a wearable pulse generator 36. The wearable pulse generator 36 produces a prescribed electric waveform and delivers it to the electrode 1. The wearable pulse generator 36 comprises a battery, a microprocessor, a step-up transformer, and an outer housing. Additionally, the wearable pulse generator 36 includes one or more connectors 38 suitable for connecting to the electrode 1. The outer housing and connectors of the wearable pulse generator 36 are substantially water resistant, permitting use in direct contact with skin during which the device may be exposed to bodily fluids. In another embodiment the incontinence treatment system 35 additionally comprises a docking station 37 that serves to recharge and/or program the wearable pulse generator 36.

The wearable pulse generator, like the electrode, is configured for extended wear, allowing the user to wear the component on his person for multiple hours and between treatment sessions-due to its size, weight and contour. In certain embodiments, the wearable pulse generator is concealable within or under the user's clothing. Similarly, maintaining a relatively small physical volume contributes to successful concealment. In one embodiment these features are achieved by using a flat battery configuration. In another embodiment this is achieved by using a planar step-up transformer. In another embodiment this is achieved by minimizing the number and size of user control features (e.g. buttons, dials, lights, graphic displays, touchpads) on the wearable pulse generator. In another embodiment the wearable pulse generator includes a user control feature that when activated acts to suspend or delay EMS treatment. In another embodiment the user controls device settings through a smart phone device via an app or web-based interface.

The housing of the wearable pulse generator includes a feature for situating the component within or under the user's clothing. In one embodiment this is a clip, latch or closure configured to interface with the user's garment along the waistline. In another embodiment the position of the wearable pulse generator is maintained with an adhesive.

In another embodiment a skin contacting surface of the housing provides a conductive region suitable for establishing current between it and a conductive region on the electrode. For example, current flows from an anode on the electrode, through tissue and to a cathode on the housing.

In one embodiment, when not being worn the wearable pulse generator is connected to a docking station that acts to recharge the battery of the wearable pulse generator. In one embodiment the docking station provides an interface through which the user can visualize and manipulate device setting including treatment waveform, intensity, and treatment schedule (e.g. when to begin treatment, for how long, how many times per day). The interface may include buttons, dials, lights, graphic displays and touchpads.

Throughout this disclosure use of the term electric muscle stimulation (EMS) is not intended to limit the scope of the invention. Similarly, differing specific terms or means of contracting targeted muscles that are considered interchangeable include functional electrical stimulation (FES), transcutaneous electrical nerve stimulation (TENS) and interferential currents (IF). Further, the terms anode and cathode are used to designate directionality of current flow. There use is not meant to limit the scope of applicable embodiments to a specific anode-cathode orientation. Rather, it is understood that in many instances the directionality of current flow could be reversed while achieving the same clinical benefit. Further, bipolar waveforms can be used such that each conductive region serves as both anode and cathode over the course of treatment.

Figure 15:
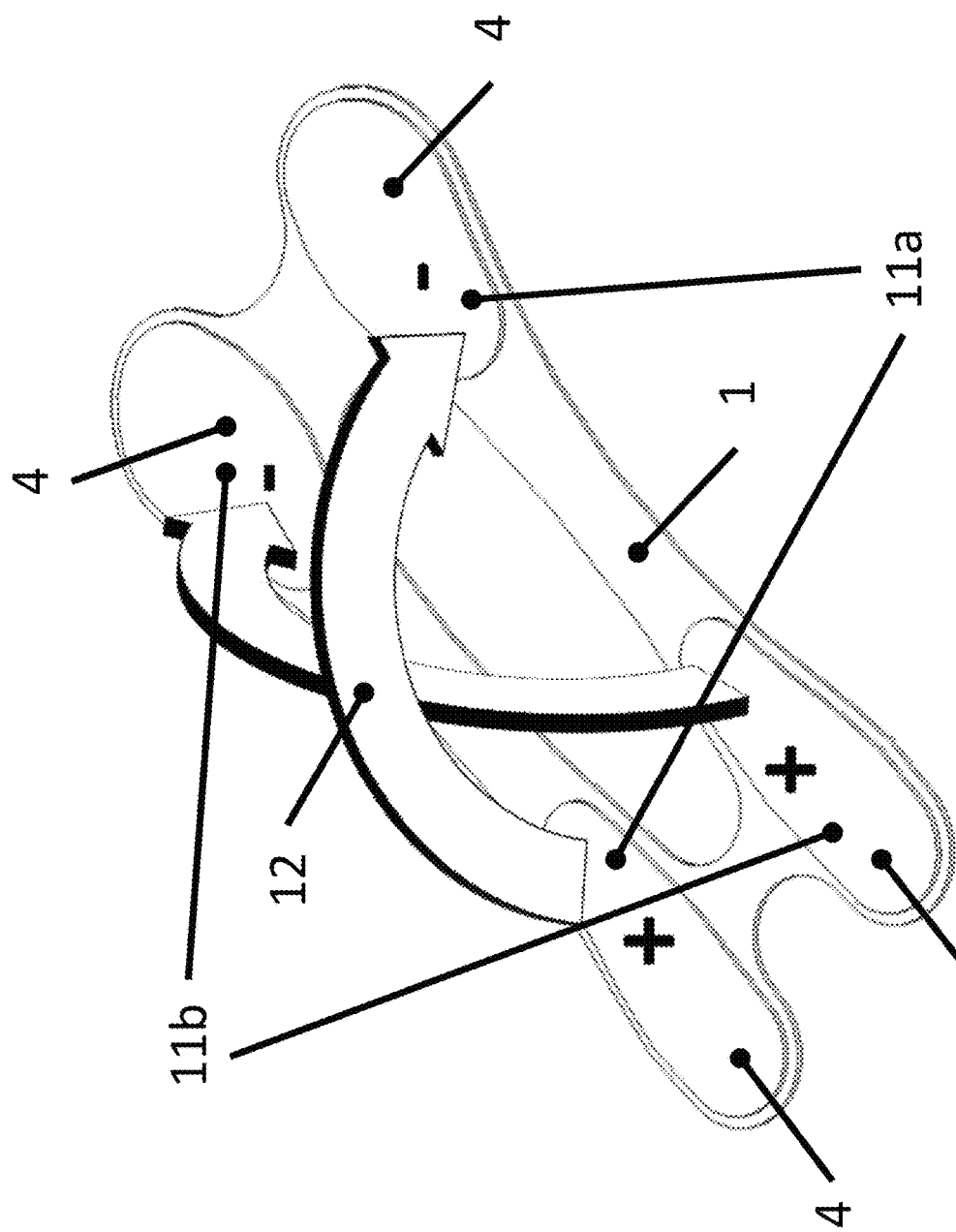
FIG. 15 is a schematic view of an electrode embodiment.

More specifically, interferential currents have been found to provide a particularly effective treatment. IF currents utilize two intersecting anode-cathode pairs operating at different output frequencies such that their resulting interference signal generates a local beat frequency at a targeted location within the tissue. The output frequencies are selected to maximize tissue penetration depth and minimize skin surface, while the beat frequency is paced to stimulate the targeted muscles. By way of non-limiting example, a first anode-cathode pair may operate at 4000 Hz and a second anode-cathode pair may operate at 4050 Hz, resulting in a beat frequency of 50 Hz. Preferred embodiments of the disclosed electrode device operating with IF current have a difference between the first and second frequencies (i.e., beat frequency) within the approximate range of 1-150 Hz. Even more preferably, IF current operating embodiments have a beat frequency within the approximate range of 20-75 Hz, with one preferred embodiment operating with a beat frequency of about 50 Hz. Referring to FIG. 15, in one embodiment electrode 1 is comprised of four conductive regions 4 forming two anode-cathode pairs 11a and 11b oriented such that their respective currents intersect 12.

Figure 16:
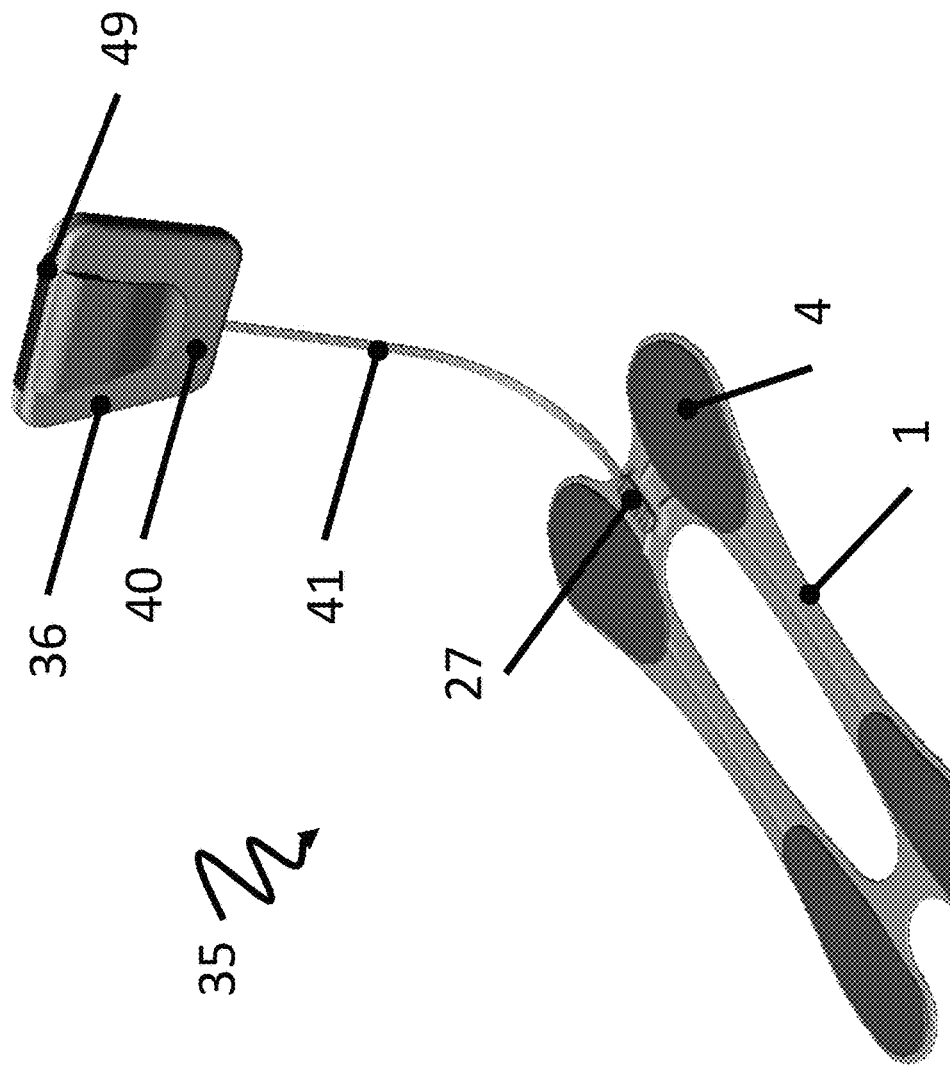
FIG. 16 is a rendering of an incontinence treatment system.

FIG. 16 shows another embodiment of the incontinence treatment system 35 comprising an electrode 1 and wearable pulse generator 36. Here the electrode 1 is comprised of four conductive regions 4. Connection between the electrode 1 and the housing 40 of wearable pulse generator 36 is achieved through cable 41. Cable 41 includes one or more connectors 27. In one embodiment at least one connector 27 forms a detachable connection with the electrode 1 or wearable pulse generator 36. In another embodiment cable 41 is detachably connected to both the electrode 1 and wearable pulse generator 36. In another embodiment the incontinence treatment system 35 is comprised of more than one cable 41 provided in different lengths suitable to accommodate a range of patient anatomies and placement locations of the wearable pulse generator 36.

Figure 17:
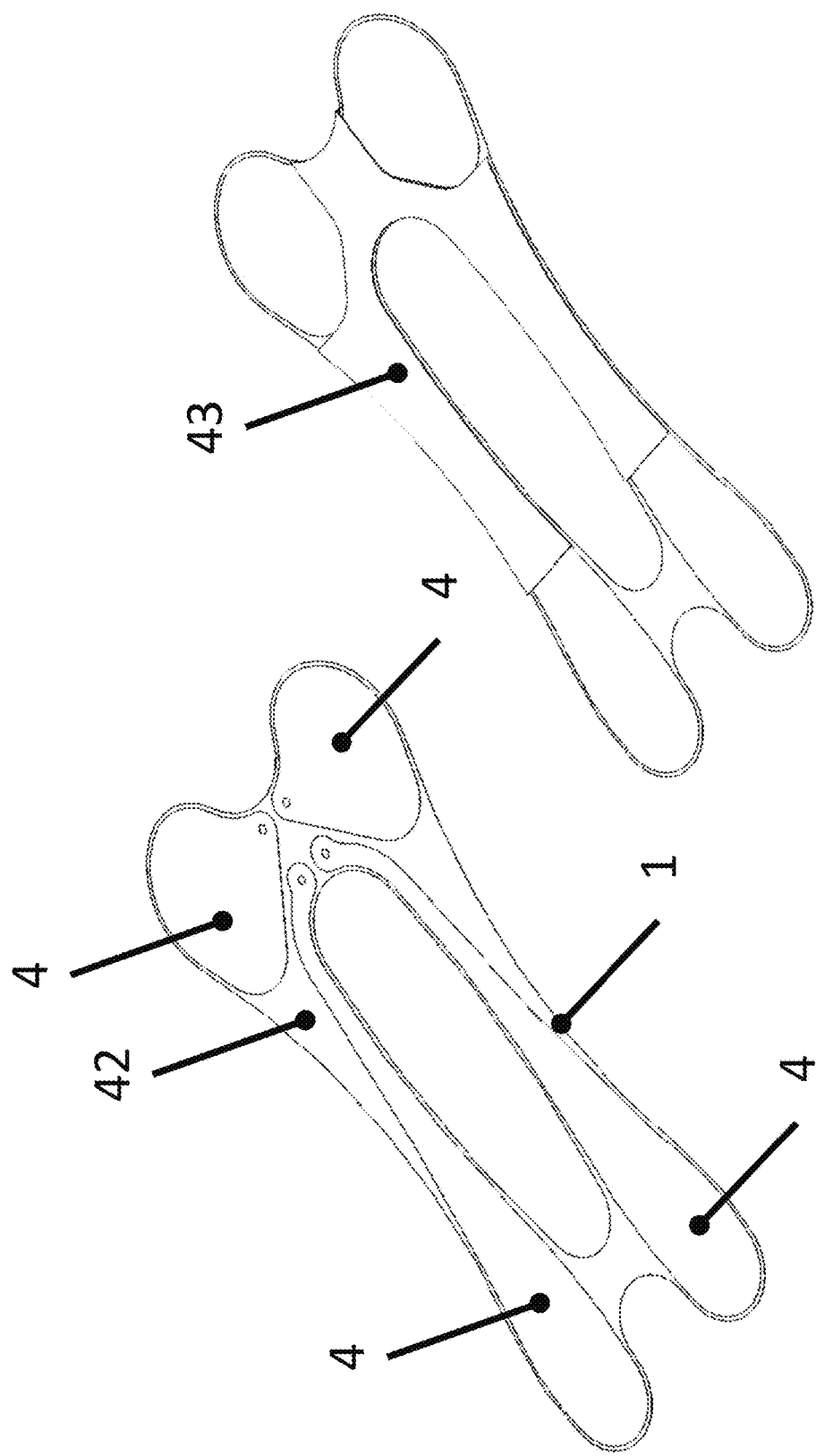
FIG. 17 provides perspective views of a multi-layered electrode embodiment.
Figure 18:
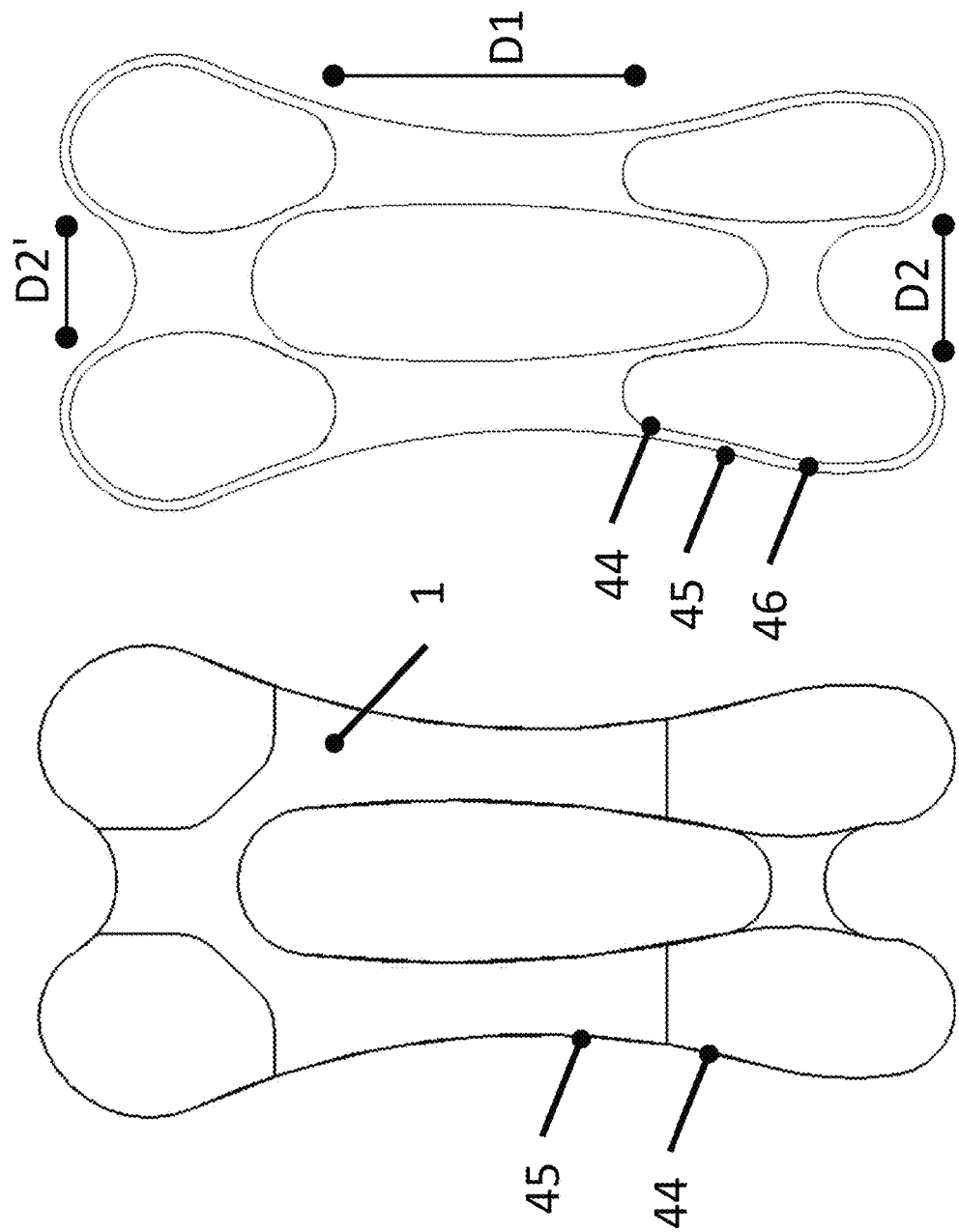
FIG. 18a and FIG. 18b are views of electrode embodiments.

FIG. 17 depicts an embodiment of electrode 1 in which four conductive regions 4 are provided on a non-conductive substrate 42. The conductive regions 4 are provided in an arrangement such that portions of each conductive region 4 are collocated and provide continuity to connector 27. In one embodiment connector 27 comprises a plurality of snap-fit button features. Further, a portion of one or more conductive regions is covered by an electrically insulating layer 43. This composition is potentially beneficial in that it eliminates the need for wires within electrode 1, thereby reducing manufacturing cost. FIG. 18a depicts an embodiment of electrode 1 with four conductive regions 4. By way of non-limiting example, the electrode has dimensions of 20 cm long by 10 cm wide, providing an electrode aspect ratio (i.e. length/width) of 2:1. Further, egress 6 has a length of 10 cm and a width of 3.3 cm, providing an egress aspect ratio of 3:1. Further, conductive regions 4 are spaced 2 cm apart in a lateral direction and 8 cm apart in the longitudinal direction. Other embodiments may have electrode aspect ratios of greater than 1.5:1, egress aspect ratios of greater than 2:1, lateral spacing of conductive regions greater than 1 cm and longitudinal spacing of conductive regions greater than 5 cm. In another embodiment one or more anterior conductive region 47 are wider than one or more posterior conductive region 48. In another embodiment one or more posterior conductive region 48 is longer than one or more anterior conductive regions.

FIG. 18a depicts an embodiment with conductive region edges 44 that are contiguous with electrode edges 45. FIG. 18b depicts an embodiment of electrode 1 wherein the conductive region edges 44 are offset from the electrode edges 45. The margin 46 defined by the space between the conductive region edges 44 and the electrode edges 45 may comprise a portion of the non-conductive region 5. In certain embodiments margin 46 is configured to isolate the conductive regions 4 from bodily fluids. In another embodiment gasket 22 is formed around the periphery of one or more conductive regions 4.

In another embodiment electrode 1 is formed as a multilayered construct wherein an electrically conducting element in continuity with a first conductive region passes under and is electrically isolated from a second conductive region. In another embodiment the electrically conducting element is a wire. In another embodiment the electrically conducting element is a layer of conductive medium.

In one embodiment of the electrode a multilayered construct includes a stiffening member proximate the conductive region 4, providing a construct with relatively more rigidity near the conductive regions 4 and relatively less rigidity near the non-conductive regions 5. In one embodiment the non-conductive region provides for a measure of elasticity.

Figure 19:
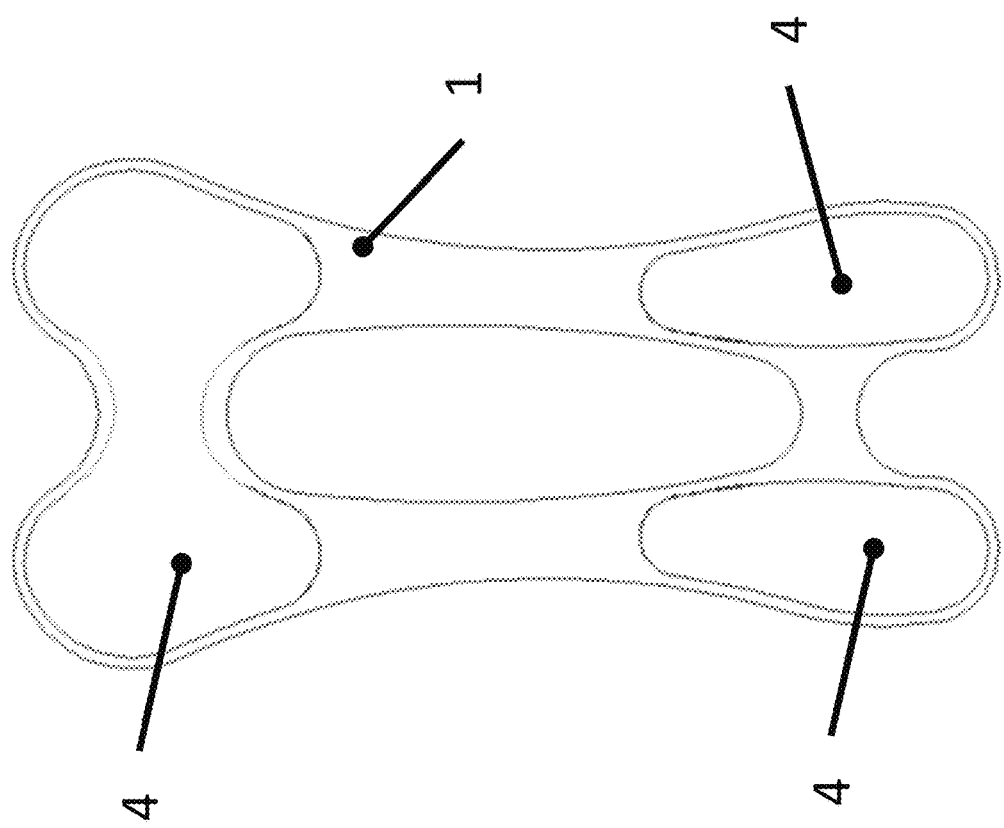
FIG. 19 is a view of an electrode embodiment.

Referring to FIG. 19, in an embodiment suitable for EMS, the electrode 1 is comprised of three conductive regions 4.

Referring back to the incontinence treatment system 35 of FIG. 16, wearable pulse generator 36 includes button 49 that serves as a means for the user to interface with the wearable pulse generator 36. The button 49 may be located on the top edge of the housing (shown) or other patient accessible surface. The button 49 may serve one or more functions selected from a group including power on, power off, defer treatment, extend treatment, increase intensity and decrease intensity. In another embodiment more than one button 49 is provided on the wearable pulse generator 36. Certain embodiments of the wearable pulse generator 36 include a rechargeable battery and means of connecting the wearable pulse generator to a recharging element.

Another embodiment of the invention includes a method for treating incontinence comprising treatment blocks during which the electrode 1 described herein is worn continuously and wherein each treatment block is comprised of sequential periods of active and inactive treatment. By way of non-limiting example, a treatment block may comprise 8 hours during which a user continuously wears the electrode 1. During this treatment block treatment (i.e. pelvic muscle floor training or toning provided by inter alia EMS, TENS, or IF) is provided in 10 minute intervals separated by 50 minutes of inactivity, during which the electrode 1 is not delivering treatment. Other embodiments include block treatment times of 1-12 hours, active treatments durations of 5-30 minutes and inactive durations of 10-120 minutes. This automated treatment method is beneficial in that is facilitates multiple treatment sessions without requiring the user to purposefully initiate each active treatment session.

In certain embodiments the duration of treatment blocks and active/inactive periods is controlled through a user interface. This user interface may comprise software accessible as a computer program or mobile device application. This software can provide the ability to track device usage across multiple treatment blocks and report data to the user or healthcare professional.

Certain embodiments of the incontinence treatment system 35 include one or more sensors proximate the outward facing surface 3 of the electrode 1 and configured to measure the moisture content of an adjacent absorbent pad. This moisture content data can be subsequently used to monitor leakage during the course of treatment, both in the short term (i.e. within a treatment block) and the longer term (i.e. between treatment blocks). In this way the user or healthcare professional can track efficacy of the treatment. Monitoring a change in electrical impendence is an exemplary means of detecting moisture. Measuring temperature change is another exemplary means of detecting moisture.

Similarly, certain embodiments may include one or more sensors proximate the skin contacting surface that monitor the presence of moisture near the conductive regions. The presence of excessive moisture in this region may adversely affect the intended electrical continuity at the skin-electrode interface. By appreciating the level of moisture content an internal algorithm can determine whether to initiate and/or stop treatment or to adjust signal intensity levels, all in an effort to provide optimal treatment and safety.

Certain embodiments may monitor bioelectric feedback to identify when and to what degree the pelvic floor muscles are contracting. This bioelectric feedback may be received through the conductive regions 4 or through separate sensor elements. This information is useful in assessing the short-term and long-term efficacy of the treatment. In one embodiment, when muscle contraction response to a given applied current falls below a set limit the treatment is concluded. In another embodiment, when muscle contraction response to a given applied current falls below a set limit the signal intensity is increased. In another embodiment, intensity level is automatically adjusted to minimally exceed the activation level of the target musculature.

In another embodiment the device is configured to be worn while the user sleeps. The corresponding treatment block delivers one or more active periods, wherein the first active period begins after the user has fallen asleep and at an intensity level that does not wake the user. In one embodiment the initiation of this first active period is controlled by a timer. In another embodiment initiation of the first active period is controlled by a sleep monitor feature that identifies when the user has fallen asleep. Such sleep monitor features are known elements of wearable wellness devices. In another embodiment the sleep monitor feature continuously monitors the user's sleep pattern and delivers multiple active treatments when the user is in the deepest sleep cycles. In another embodiment, prior to going to sleep the user executes a program that confirms suitable placement and intensity level settings of the device such that when the device enters the first active period it will deliver treatment per intent. In another embodiment, the treatment starts before the user has fallen asleep.

In a similar manner, the incontinence treatment system 35 can monitor impedance through the conductive regions before, during and after active treatment. Changes in impedance can be used to determine whether one or more conductive regions has diminished skin contact. When this occurs, the system can stop or prevent treatment and signal the user to modify placement of the electrode.

In another embodiment, appreciating that less activation energy is required to contract toned muscles, the system monitors the intensity of muscle contraction as a function of signal intensity. This data can then be used to quantify the response to treatment both within a treatment block and between treatment blocks. Further, this data may be used to auto adjust the signal intensity level provided by the signal generator.

Figure 20:
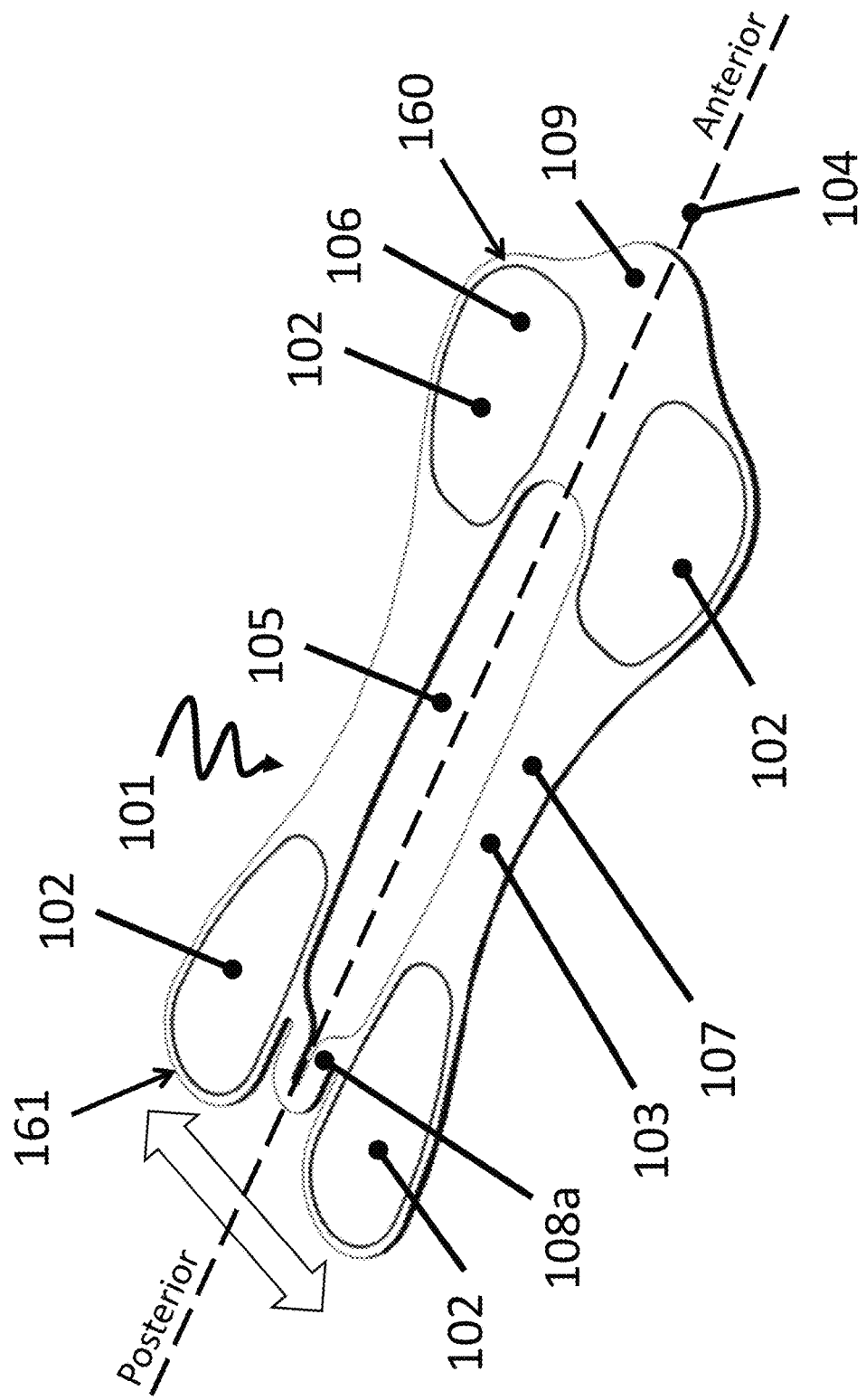
FIG. 20 is a perspective view of another embodiment of an electrode viewed from the patient-contacting side.

Referring to FIG. 20, an embodiment of the electrode or electrical stimulation device 101 with lateral adjustability is depicted. This embodiment of the electrode 101 comprises two anterior and two posterior conductive regions 102 located on the patient contacting side 103 of the body—two spaced posterior conductors in the tail portion 161 of the body and two spaced anterior conductors in the head portion 160 of the body. The electrode 101 has substantial symmetry about a mid-sagittal plane, depicted as a bisecting axis 104. Like the embodiments depicted above, an opening in the body defines a longitudinally extending void space 105 extending rearwardly or posteriorly from an intermediate position (i.e., longitudinally between the head and tail) in the body 103, which splits the tail portion into left and right sides. In this and previous embodiments, the electrode longitudinally-extending void space 105 is in the form of a central egress 105 positioned substantially along a bisecting axis 104 for providing a pathway for excretion of bodily fluids from the urethral or vaginal openings. The conductive regions 102 may comprise a conductive substrate and a conductive hydrogel 106. Typically, the hydrogel 106 has mild adhesion properties to help maintain contact of the conductive region 102 against the patient's skin without use of straps, belts or other means. Non-conductive regions 107 of the patient contacting side may include foam and may also be lightly adhesive.

As shown, near the posterior end or tail portion of electrode 101, a non-conductive expandable section of web material 108a allows lateral expansion and/or contraction between the respective spaced apart posterior conductive regions 102 for ease of use and placement, while simultaneously allowing them to reciprocate independently from one another. Independent movement or reciprocation of the posterior conductive regions allows a user to define a comfortable spacing during device application, as well as allows the patient to move freely, without the device restricting motion. In a preferred application, the posterior conductors are positioned proximate a patient's buttocks region toward the legs, so the described independent movement allows the patient to continue normal activities such as walking and other movement. Further, the existence of the web material as a limit on the extend of posterior regions has shown to assist in placement of the posterior conductors on a patient.

Figure 21:
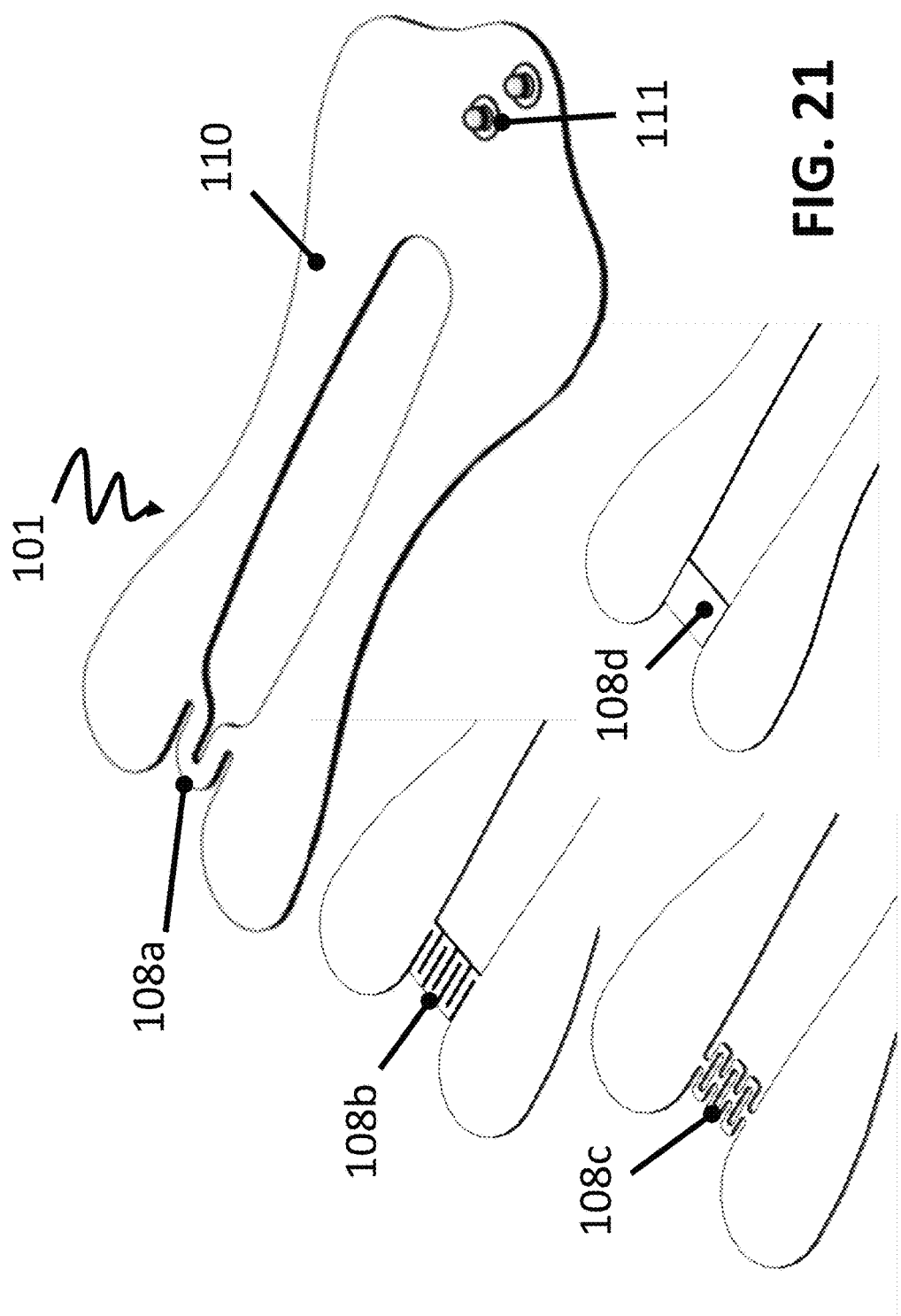
FIG. 21 shows optional alternate embodiments of a lateral expansion and adjustment feature of an electrode according to the disclosure.

As depicted in FIG. 20, the laterally expandable section 108a can take a generally serpentine shape. Alternate configurations of expandable section are depicted in FIG. 21. The expandable section 108b is defined by multiple parallel slits or slots located on opposing side of the web of material. The expandable section 108c is defined by multiple slits or slots, some of which extend to the extents of the web and some of which do not extend to the extents. When laterally expanded the slits or slots deform and take on a more circular or rectangular shape. The specifically depicted examples of the expandable sections are not meant to be limiting. Further, the depiction and description of slits and slots is not intended to limit the feature to a specific shape or method of fabrication. The expandable sections 108a-c notably do not limit relative movement of the posterior conductive regions in a direction closer to one another, but the geometry of them does typically limit the relative movement in other directions (e.g. <1 cm, <2 cm, <3 cm, <5 cm, <10 cm). Additional embodiments exist with expandable section (similar to those depicted as reference numerals 108a, 108b, 108c, 108d, 146, 211 or 212) that is a separately attachable and detachable member, rather than integrally incorporated into the body of the electrical stimulation device.

In certain embodiments expandable sections 108a-c are constructed of a non-elastic material and relative motion of the posterior conductive regions is permitted by bending, buckling, or opening. In an alternate construction of lateral expandable sections 108a-d the web of material connecting right and left posterior conductive regions 102 is constructed of an elastic material. In this configuration the feature may or may not utilize feature geometry as a means of facilitating expansion. The elastic material may be incorporated as a separate component and connected to non-elastic features proximate the posterior conductive regions 102. Alternately, the elastic material may be present in both expansion feature 108a-d and other features of the electrode (e.g. a substrate for the conductive ink circuit, a patient contacting dielectric layer). While expandable, the sections 108a-d also provide a beneficial limit on the extent of lateral reciprocation between the respective spaced apart conductors.

At the anterior end of electrode 101, a tab 109 provides a region for the user to grasp electrode 101 during placement and removal. The patient contacting side 103 of the tab 109 is typically free from hydrogel 106 or any adhesive material, thereby facilitating patient handling. The shape of electrode 101, which gradually widens through the tab 109 region moving anteriorly to posteriorly (i.e. without an abrupt edge), facilitates controlled removal the device from the skin.

Figure 22A:
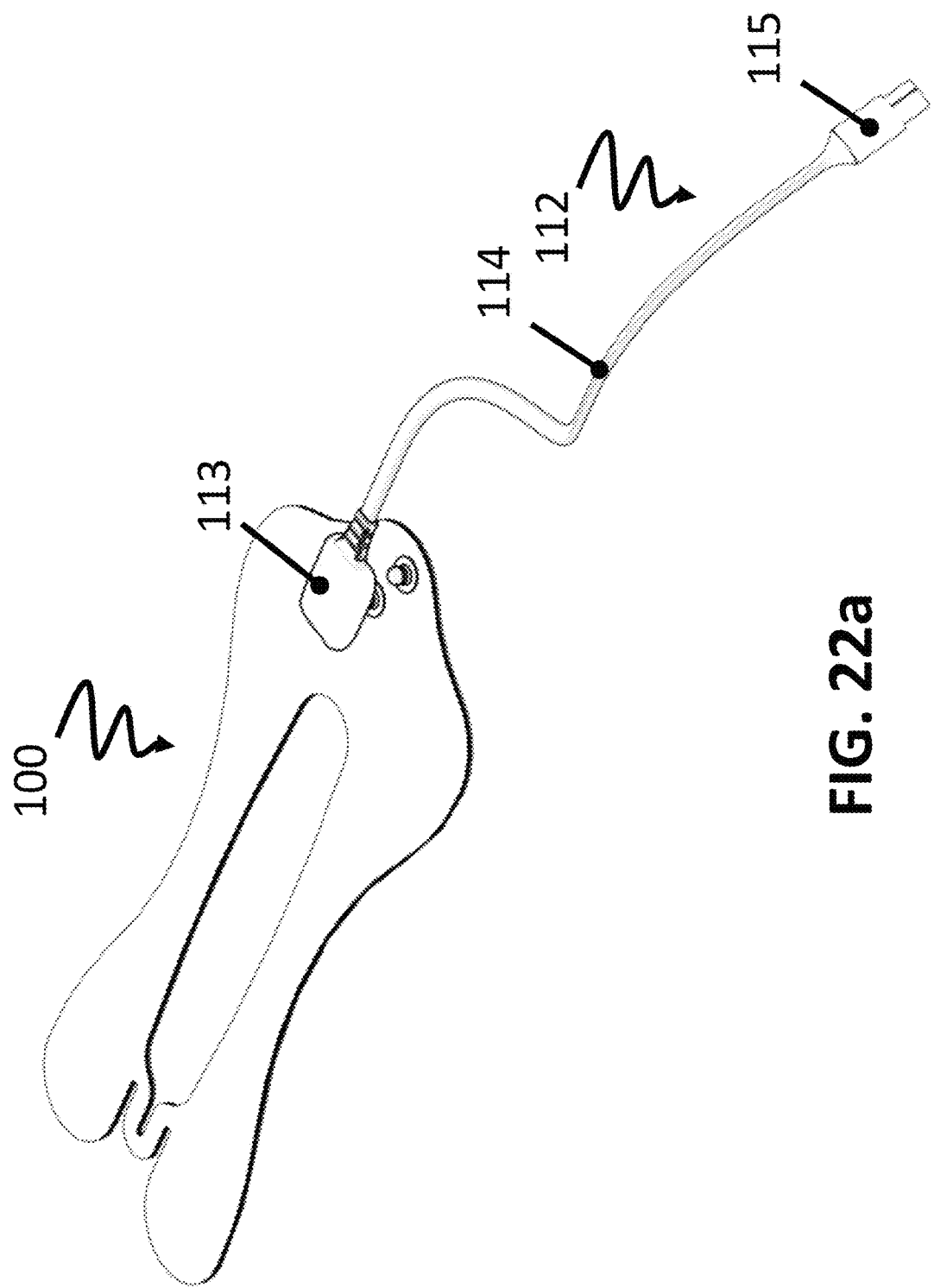
FIG. 22a is an exploded view of an electrode showing a removable medical cable assembly.
Figure 22B:
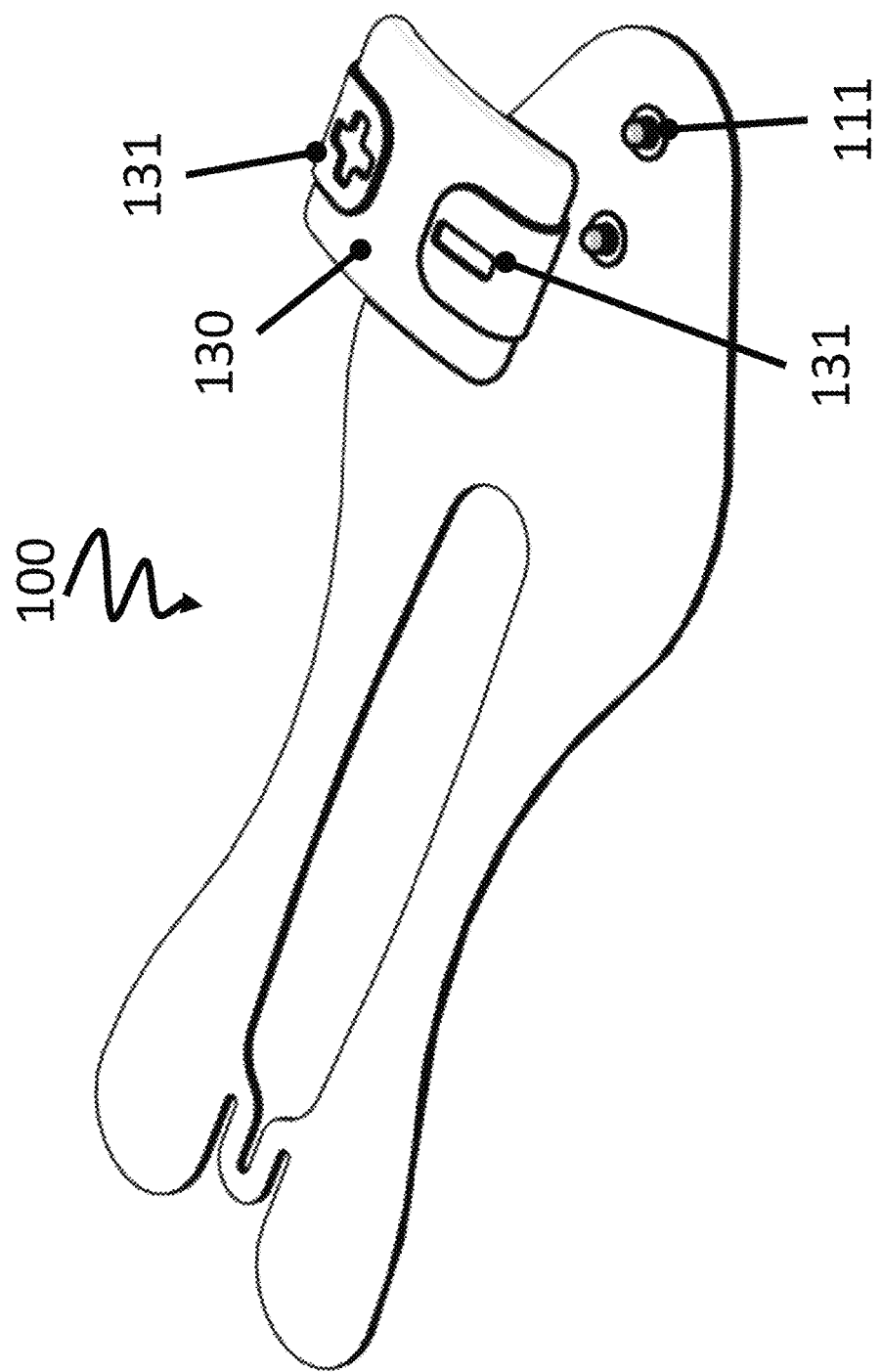
FIG. 22b is an exploded view of electrode and stimulator showing a detachable current generator.

FIG. 21, FIG. 22a and FIG. 22b depict an embodiment of the outward facing surface 110 of an electrode like those shown throughout, including element 101. The outward facing non-contact surface 110 is non-conducting, with the exception of studs or snapping members 111, which provide an electrical and mechanical connection to an electrical current generator, which can be in the form of a medical cable 112 or stimulator 130. A preferred embodiment of studs 111 is a geometry that provides a snap-fit connection. In another embodiment the connection can be formed or assisted via one or more magnets or components fabricated from ferromagnetic material. Referring to FIG. 22a, one end of medical cable 112 comprises electrode connector end 113 with receptacles (not visible) shaped to mate with studs 111. Wires 114 provide sufficient length (for example, approximately 0.25-2.0 feet) to extend from electrode 101, worn in the perineal region, to a stimulator, worn proximate the patient's waist. Wires 114 comprise multiple conductors. Stimulator connector end 115 provides a connection means to a stimulator. Referring to FIG. 22b, directly applied stimulator 130 has a low profile such that when affixed to studs 111 with receptacles (not visible) it can be worn under a patient's clothing. Controls 131 (i.e. buttons) for directly applied stimulator 130 may be provided on the front surface of the device to facilitate actuation through clothing.

In one embodiment the design of studs 111 of electrode 101 permits repeated connection and disconnection with medical cable 112 or directly applied stimulator 130. In an alternate embodiment the act of disconnecting medical cable 112 or directly applied stimulator 130 affects a structural change to studs 111 or another element of electrode 101 that prevents reuse of disconnected electrode 101, and thereby necessitating that the user utilize a new, previously unused electrode 101. Exemplary means of functionally disabling electrode 101 include provision of a feature that initiates tearing of a portion of electrode 101.

Hydrogel 106 employed within and for use with the embodiments of the disclosed electrodes is available in a variety of chemistries formulated to provide specific adhesive and conductive characteristics. Certain hydrogels are produced in sheet form and then cut to shape as part of the device fabrication process. Other hydrogels are dispensed onto a device in liquid form and later cured to obtain gel characteristics. In a preferred embodiment liquid hydrogel is dispensed on the conductive regions and cured using UV light. The hydrogel is poured to a thickness of 0.75 mm or greater, and in a particularly preferred embodiment, to a thickness of as much as 1.5 mm or greater. This hydrogel depth provides increased patient comfort relative to sheet formed hydrogels that are not as thick. Preferably, the hydrogel has a thickness great enough such that the outer surface of the hydrogel lies above the surface of the foam portion of the body of the electrode. Increased patient comfort is realized in several ways. The thick layer of hydrogel acts as a compliant layer that promotes independent movement of the skin relative to the device. Also, the thicker layer of hydrogel promotes less painful removal of the device from skin with hair. In another embodiment hydrogel 6 is poured to a thickness of 2.0 mm or greater. In yet another embodiment hydrogel 6 is poured to a thickness of 2.5 mm or greater. In one embodiment, the profile of the foam defines wells that serve to contain hydrogel prior to UV curing. However, additional embodiments exist wherein the hydrogel portion extends further, in some cases to the outer edge of the body (see FIG. 18a, for example).

Figure 23:
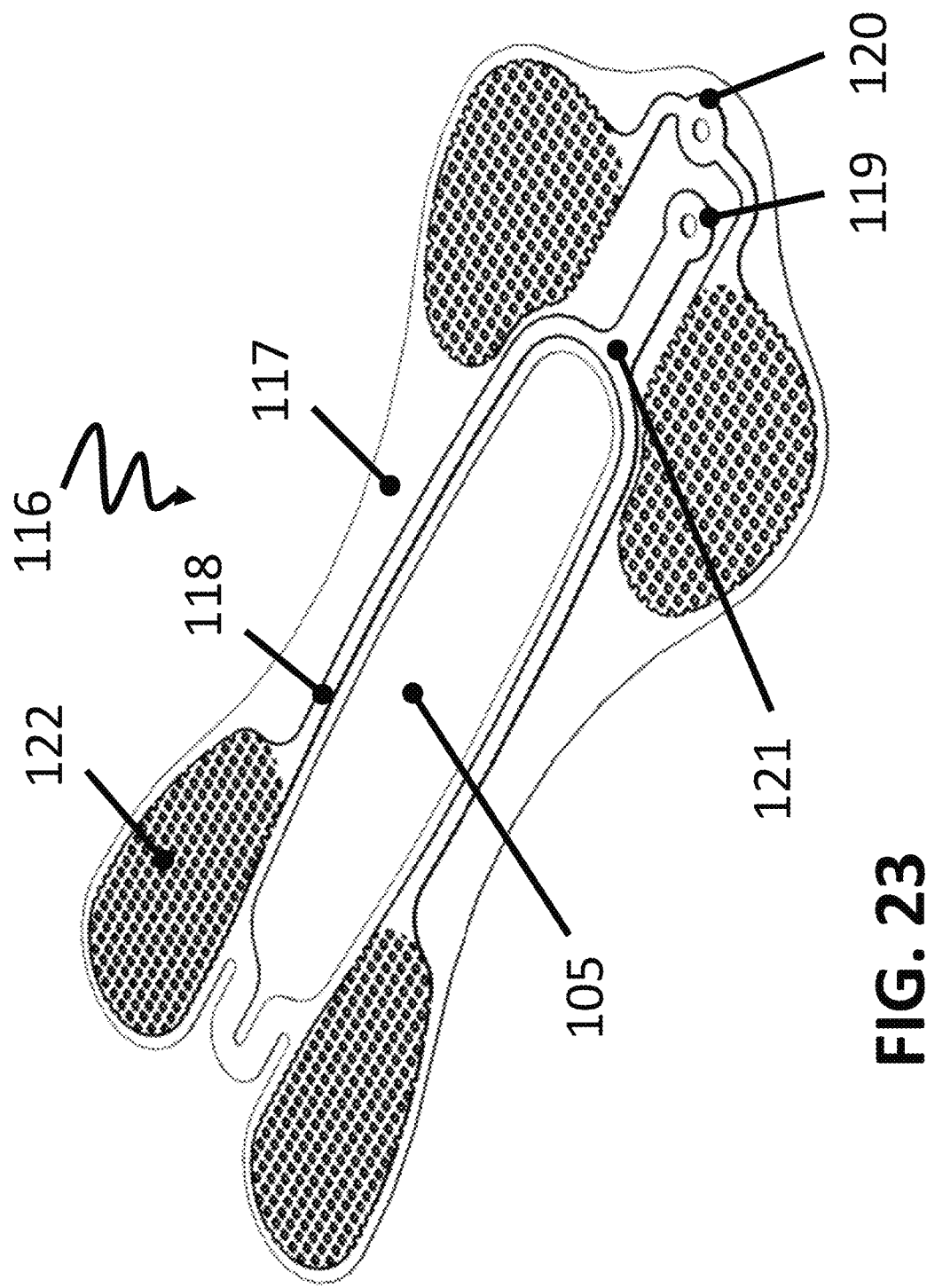
FIG. 23 shows a printed circuit layer of an electrode according to the disclosure.

FIG. 23 depicts a layer with a printed circuit 116 within electrode 101. The printed circuit 116 comprises substrate 117, which is typically formed from a thin film of a non-electrically conductive material (e.g. polymers, fabrics). One or more layers of electrically conductive ink are applied (e.g. printed) to substrate 117 to create the local electrical tracing 118 defining an electrically-conductive path for current to flow from a current generator, such as, for example, those depicted as reference numerals 113 and 130. The embodiment of FIG. 23 depicts two separate tracings, a first tracing 119 spanning from the anterior end of printed circuit 116 to the posterior conductive regions, and a second tracing 120 spanning form the anterior end of printed circuit 116 to the anterior conductive regions. In some embodiments tracing 118 may include a junction 121 that allows current to flow to separate conductive regions. Junction 121 is of particular benefit in allowing tracing 118 to accommodate the presence of the void space 105. The tracing proximate conductive regions 102 may take the form of grid region 122, providing electrical continuity to all portions of conductive regions 102 without depositing conductive ink over the entire area. This is advantageous in that it reduces the volume/mass of conductive ink required to fabricate printed circuit 116. Various grid patterns (i.e. line widths, spacing widths) are considered for grid region 122 and fall within the inventive scope of the disclosed embodiments. Additionally, other patterns of conductive ink can yield similar continuity over the entire area of the conductive region, such as for example, spiral, zig-zag, connected circles or ovals, and additional interlocking patterns. Grid region 122 may comprise a peripheral solid ring of conductive ink (not shown) that provides an uninterrupted path of electrical continuity around grid region 122.

Fabrication of electrode 101 utilizing printed circuit 116 allows for a low profile device construction and production using roll-to-roll converting equipment. Alternate embodiments of electrode 101 may utilize conventional wires instead of conductive ink tracings. In such embodiments the wires extend from the conductive regions 102 to studs 111 and are contained between substrate 117 and a layer of material (e.g. foam) comprising non-conductive region 107.

Figure 24:
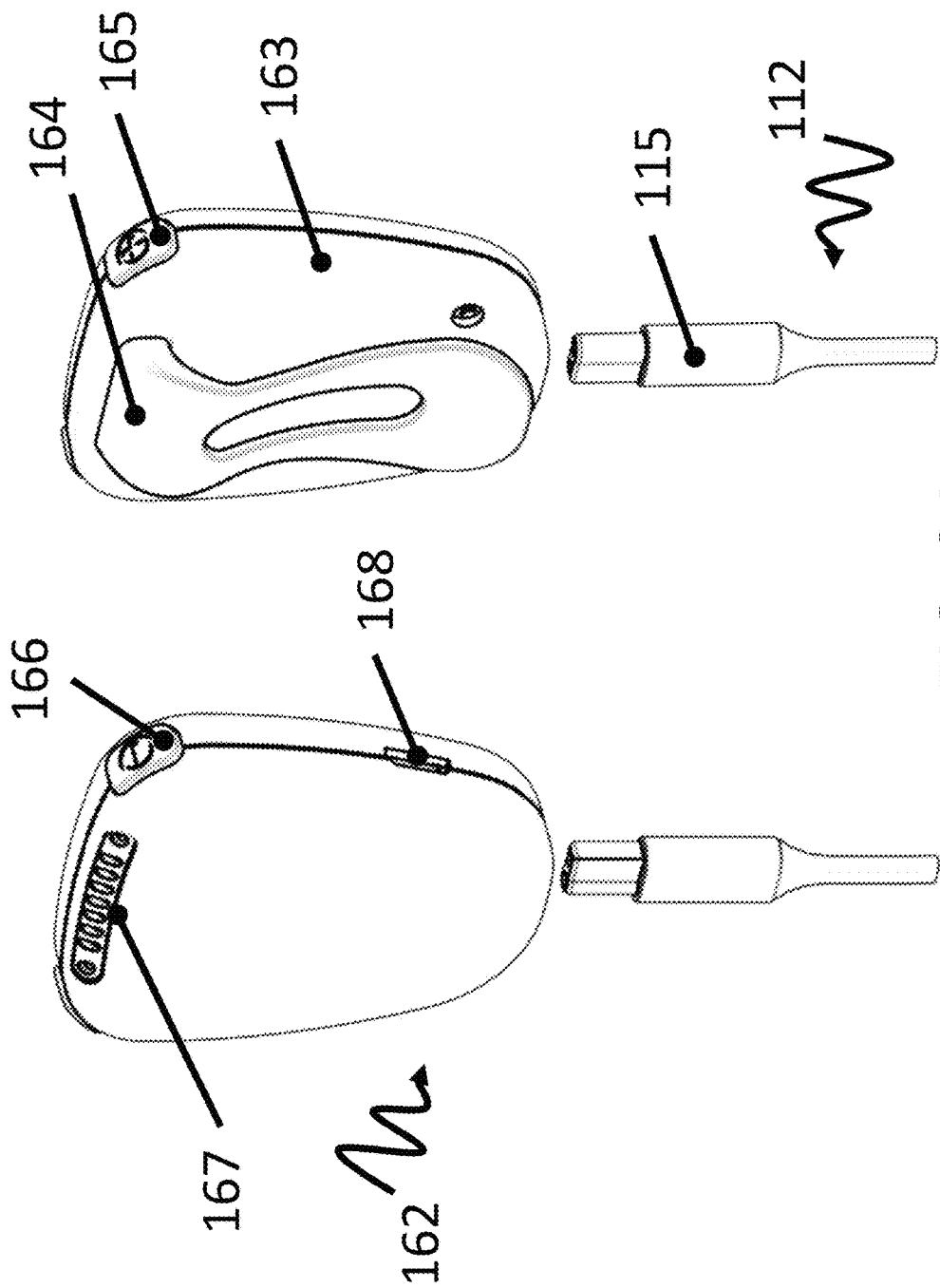
FIG. 24 show perspective views of stimulator for use with any of the electrode embodiments disclosed herein.

FIG. 24 depicts a representative embodiment of a stimulator 162 for use with any of the disclosed embodiments of the electrode for generating an electrical muscle stimulation signal. The stimulator 162 comprises housing 163 that protects electrical components including a battery and printed circuit board. This embodiment comprises elements including belt clip 164, intensity increment button 165, intensity decrement button 166, light array 167 and dual charging/data port 168. Medical cable 112 connects to stimulator 162 by inserting stimulator connector end 115 into a jack in stimulator 162 (not shown).

Figure 25:
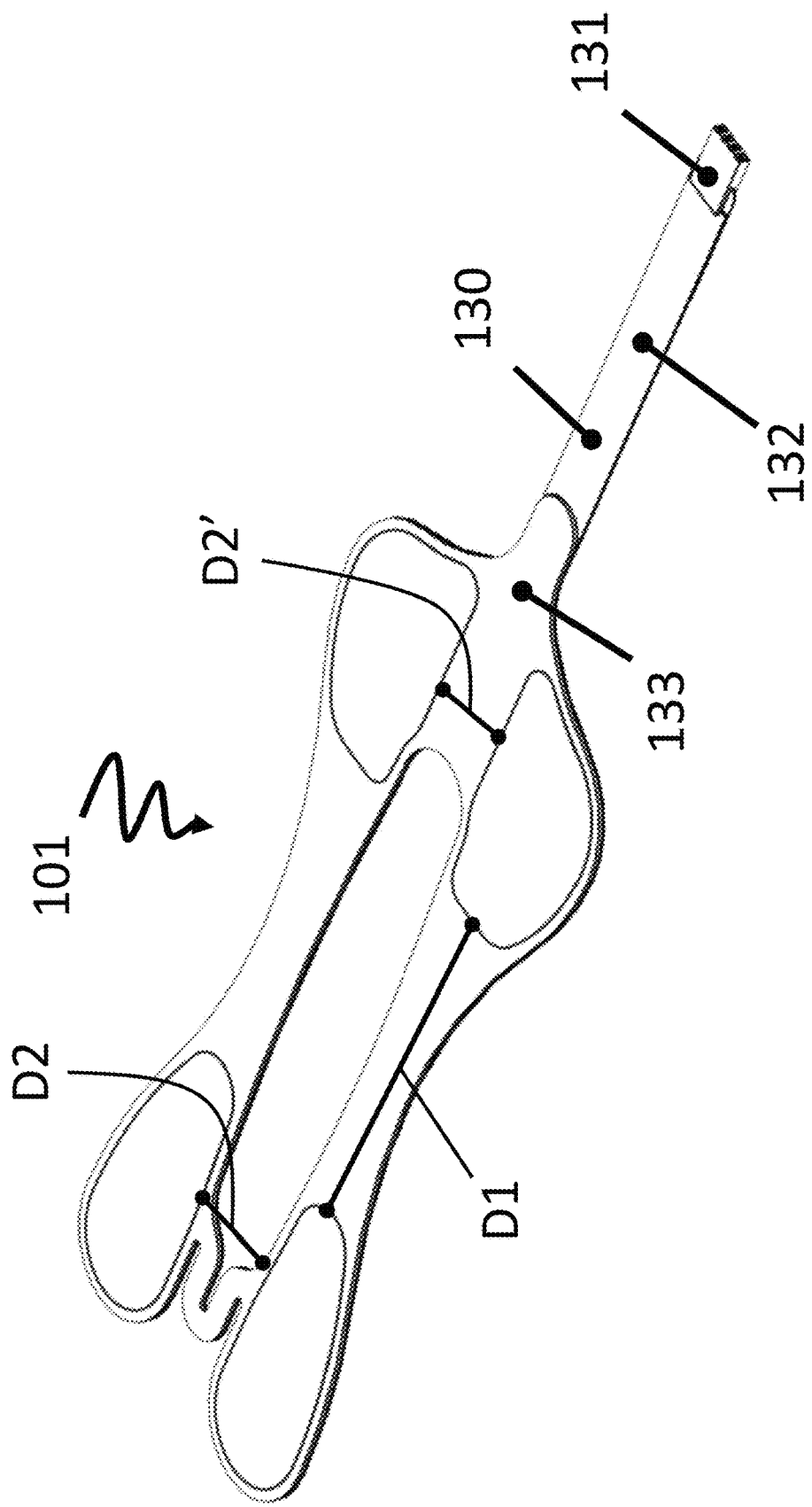
FIG. 25 shows an embodiment of an electrode with an integrated finger.
Figure 26:
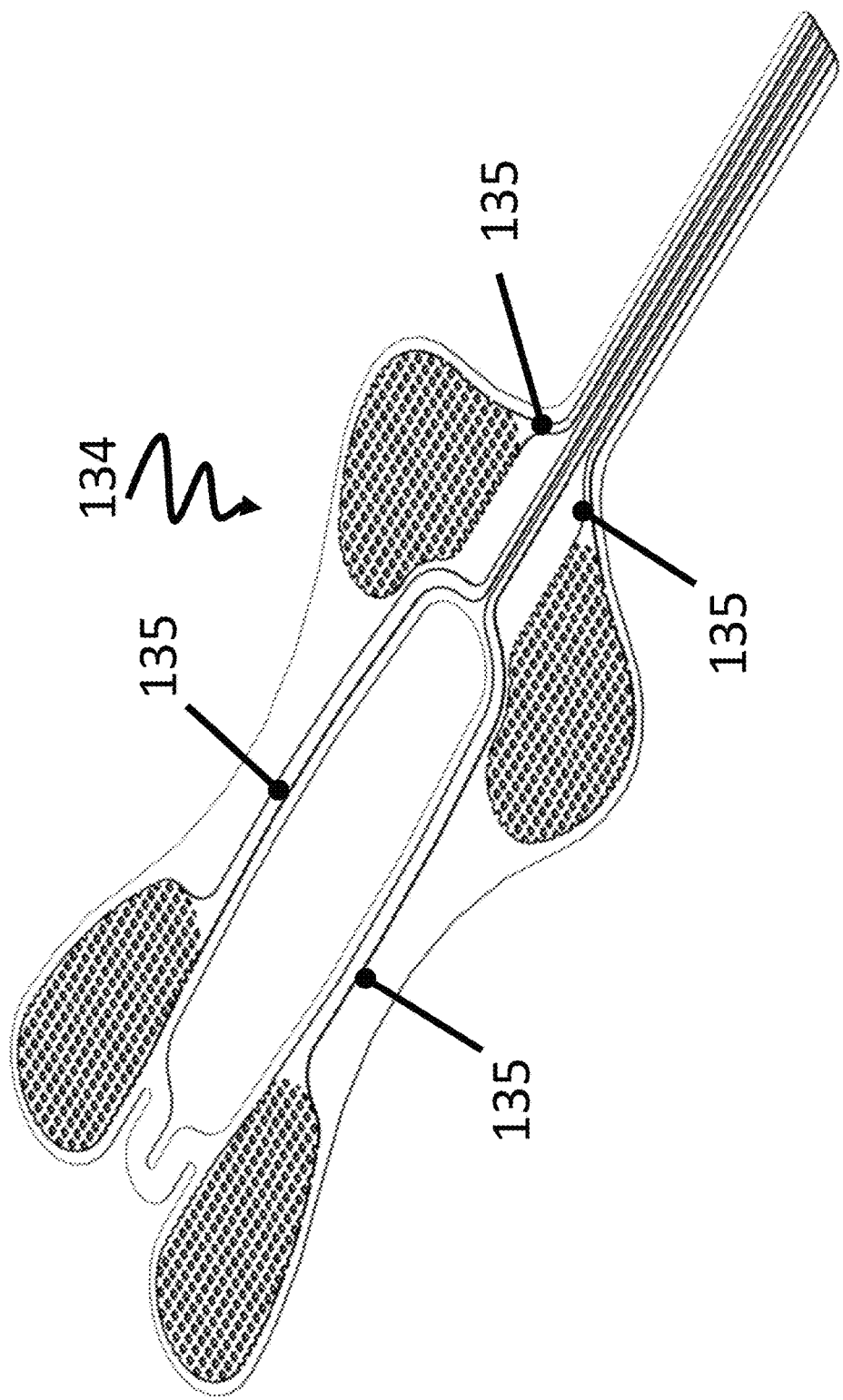
FIG. 26 shows the printed circuit layer of an electrode like that shown in FIG. 25.

FIG. 25 and FIG. 26 depict another embodiment of the invention in which electrode 101 includes an integrated "finger" 130 approximately 0.25 feet to 1.5 feet in length. The finger 130 terminates in stimulator connector end 131. In this embodiment a printed circuit 134 comprises four tracings 135 that extend from the four conductive regions to the anterior end of the device, running parallel to one another along the length of the finger 130. Tracings 135 along the length of finger 130 are covered by dielectric 132, which provides an electrically insulating layer that prevents unwanted patient contact with tracings 135. This insulating layer may extend to cover other regions of printed circuit 134, excluding the conductive regions. Foam layer 133 provides insulating properties and a soft, cushioned surface in contact with the skin.

The embodiment of FIG. 26 comprises four separate tracings 135 electrically connected to different points in the circuitry of the stimulator (like in FIG. 23. When applied to the patient, this configuration allows for delivery of a signal between pairings of electrodes, and additionally for resistivity to be measured across two conductive regions. The device monitors this resistivity through the course of a treatment session. Changes in the resistivity may indicate reduced contact of a conductive region to the skin, dehydration of the hydrogel, a discontinuity in the trace, or an increase in moisture (e.g. a urine voiding event). By monitoring resistivity changes between multiple conductive regions pairings the stimulator systematically determines which conductive region(s) has experienced the change. Upon reaching a determined threshold the stimulator may execute a variety of responsive action(s) including, for example: pausing treatment, informing the user of the issue, instructing the user to make an adjustment to the device, recording occurrence of the event, and adjusting the treatment intensity through one or more conductive region pairs. Changes in resistivity may also be monitored between treatment sessions. These changes may additionally indicate a change to the positioning of the electrode, a change in patient weight, or a change in skin preparation. As with within-treatment resistivity changes, the stimulator may execute responsive actions similar to those listed. This functionality, wherein a change in resistivity is followed by a responsive action, is applicable to all of the configurations disclosed herein, including configurations with two, three or four conductive regions. Further, the device could be constructed to monitor other electrical measures including, but not limited to impedance, conductance, current or voltage instead of resistivity while realizing similar benefits.

Figure 27:
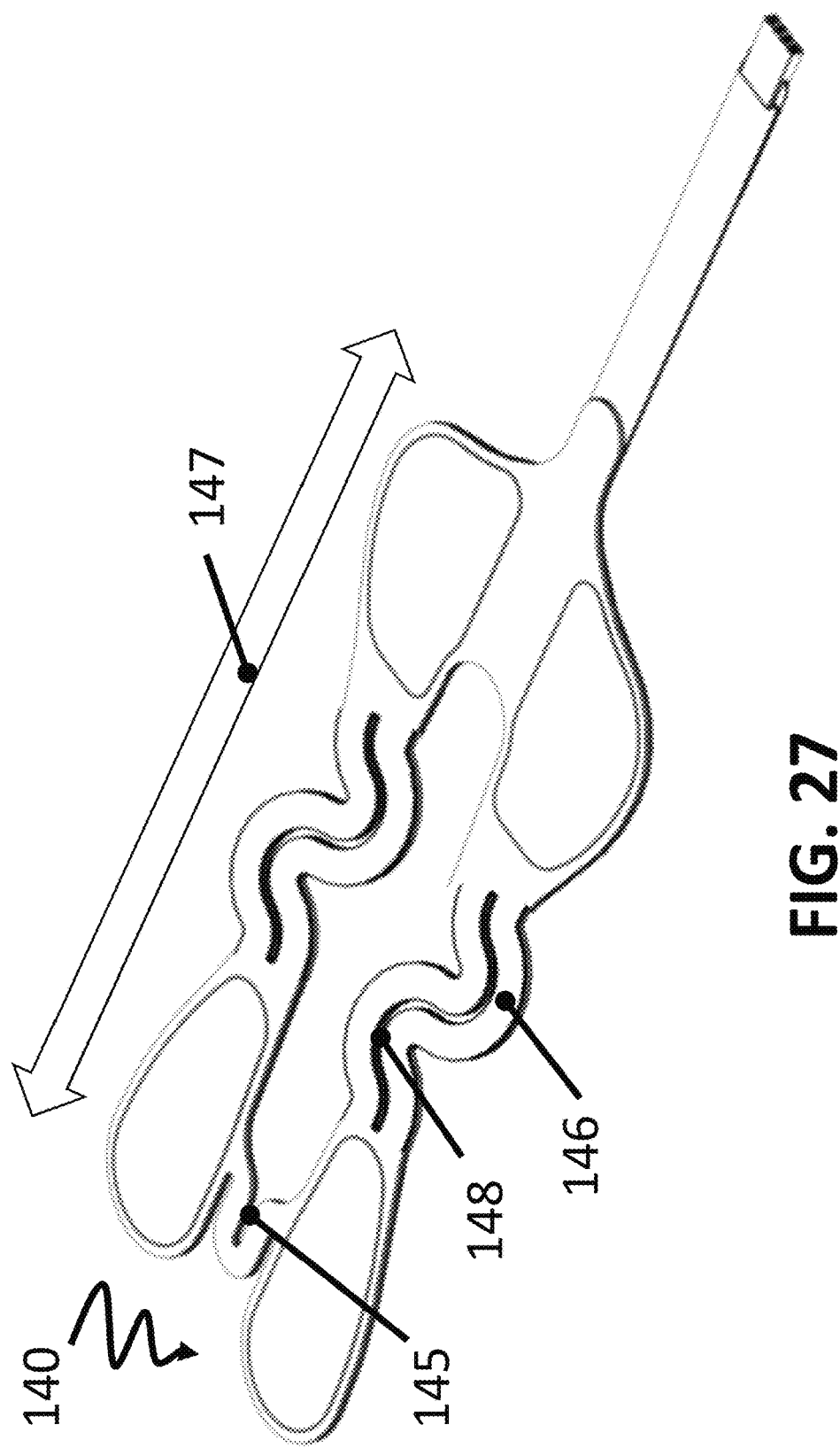
FIG. 27 is a perspective view of a representative electrode showing an anterior/posterior expansion feature.

FIG. 27 depicts another embodiment in which electrode 140 comprises lateral expandable section 145 (similar to reference numeral 108a) and longitudinal expandable sections 146, allowing reciprocation in the anterior/posterior direction. The longitudinal expandable sections 146 may take the nominal serpentine shape, and under force 147 the sections 146 extend to achieve increased spacing between the anterior and posterior conductive regions. In certain embodiments, slit 148 may be beneficial in achieving anterior to posterior expansion without substantial buckling or twisting of electrode 140 through that region.

Figure 28:
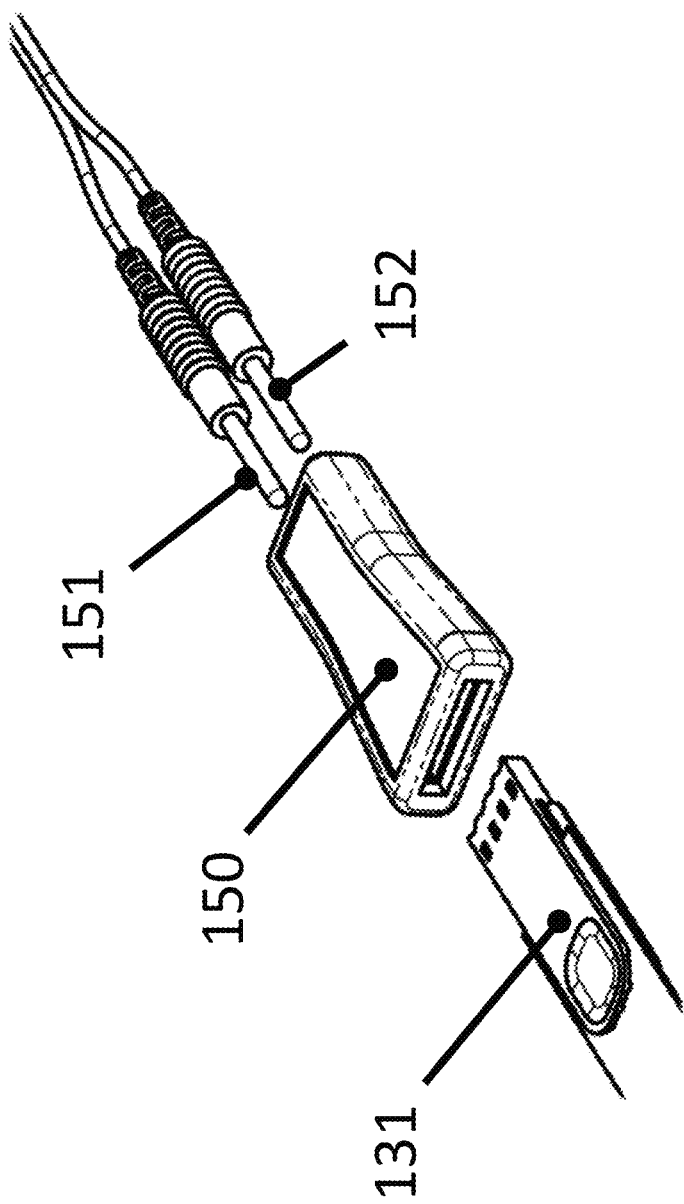
FIG. 28 is a perspective view of adapter for use with any of the embodiments of the disclosed electrode.

FIG. 28 depicts adapter 150 which is used to provide electrical connection from electrode 101 to an electrical muscle stimulation device with cables that terminate in pins 151 and 152. The adapter 150 comprises receptacles on opposing ends, one to receive stimulator connector end 131 and the other to receive pins 151 and 152. In one embodiment internal wiring of adapter 150 electrically connects first pin 151 to two tracings 135 of printed circuit 134. Similarly, a second pin 152 connects to two other tracings 135 of printed circuit 134. In this way a single-channel (i.e. two wires) electrical muscle stimulation device can be coupled to the four conductive regions of an electrode like those represented by reference numerals 101 and 140, for example. Other embodiments of an adapter comprise different numbers of receptacles on the electrode and stimulator end, for example 4 to 4, 2 to 2, or 3 to 2.

Figure 29:
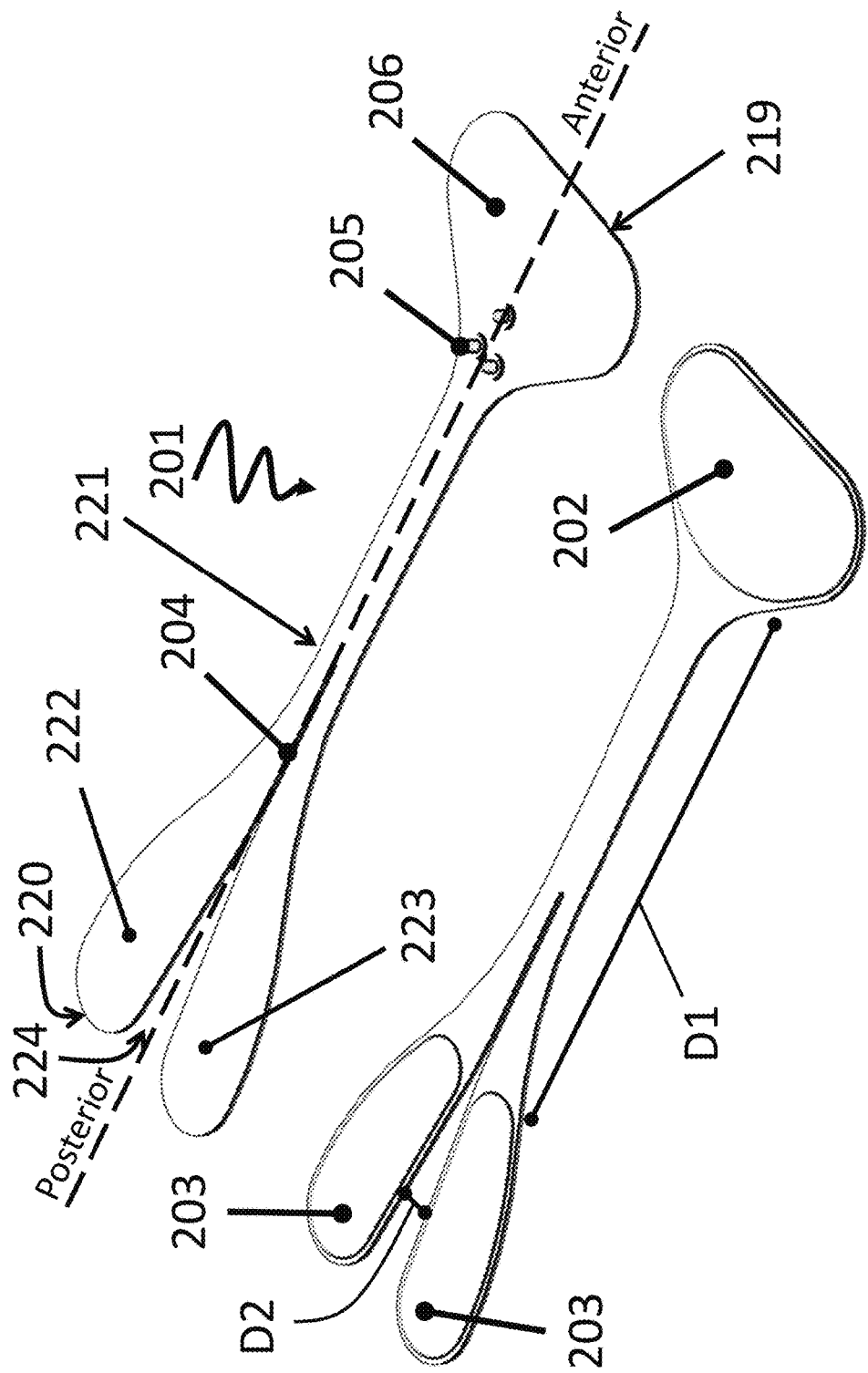
FIG. 29 shows another embodiment of an electrical stimulation device or electrode according to the disclosure.

FIG. 29 depicts another embodiment of the invention in which the electrode 201 does not include a central egress in its intermediate portion for bodily fluids to pass through. As shown, this embodiment of the electrode 201 is further defined by a single anterior conductive region 202 in a head portion 219 of the body and posterior conductive regions 203 positioned on the tail portion 220 of the body. An opening 204 extends longitudinally toward the posterior or trailing tail end 220 from an intermediate portion of the body 221. In this manner, the opening splits the tail end 220 into a right portion 222 and a left portion 223, allowing independent movement of conductive regions 203 respectively disposed on the left and right portions with void space 224 between them. Like earlier disclosed embodiments, studs or snapping members 205 on outward facing surface 206 of the electrode 201 provide an electrical and mechanical connection point for a medical cable or other current generator (not shown). FIG. 29 depicts three studs 205 corresponding to the three conductive regions, with each stud connected to an individual conductive region via a separate electrical trace (not shown). An alternate embodiment comprises two studs 205 with one stud traced to both of the posterior conductive regions and one stud traced to the anterior conductive region. In all embodiments of the electrical stimulation device disclosed herein, there is no limit on the minimum lateral void spacing. As discussed, the void space in the body is configured mostly to allow passing of bodily fluid from the individual or animal receiving treatment and/or to allow the individual or animal to move freely when the device is attached and in position for treatment. Further, as is clear from the herein description and the depicted embodiments, the void space need not be uniform or parallel in either the lateral or longitudinal direction. For example, the void space can be 5 to 100 mm long. An exemplary embodiment includes void space of between 10 to 30 mm long]. Typically, these exemplary sizes of the void space are to the "as worn" state on a patient, rather than the free-standing flat device prior to application to the patient.

Figure 30:
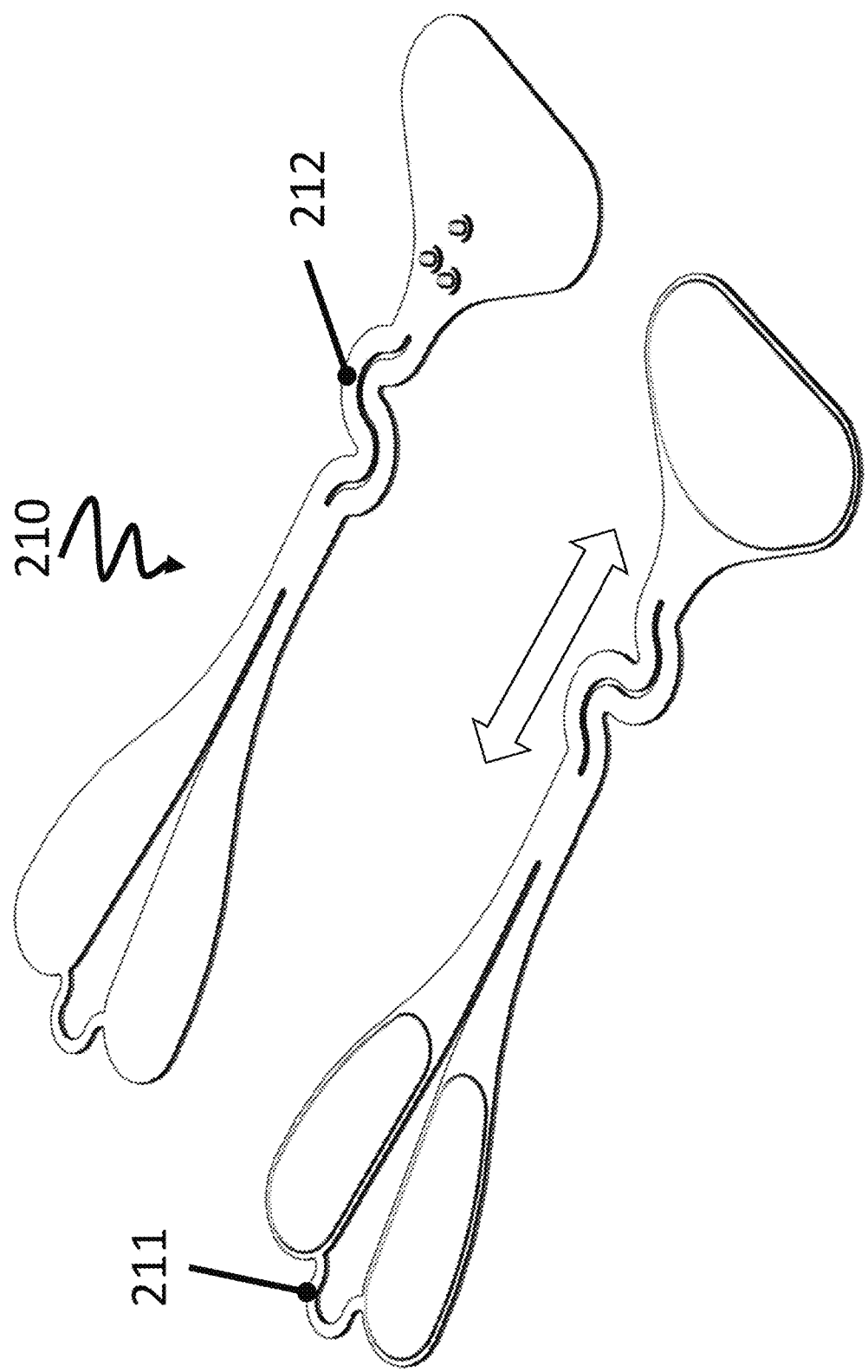
FIG. 30 shows another embodiment of an electrode like that depicted in FIG. 29 with anterior/posterior expansion features incorporated therein.

FIG. 30 depicts an embodiment with a lateral expandable section 211 for limiting the relative movement between the two posterior conductive regions in the lateral direction, and a longitudinal expandable section 212 that allows the user to reciprocate the longitudinal distance between the anterior and posterior conductive regions. The lateral and longitudinal expandable sections, 211 and 212, operate similarly to those shown in FIGS. 21 and 27 as included in other embodiments.

Figure 31:
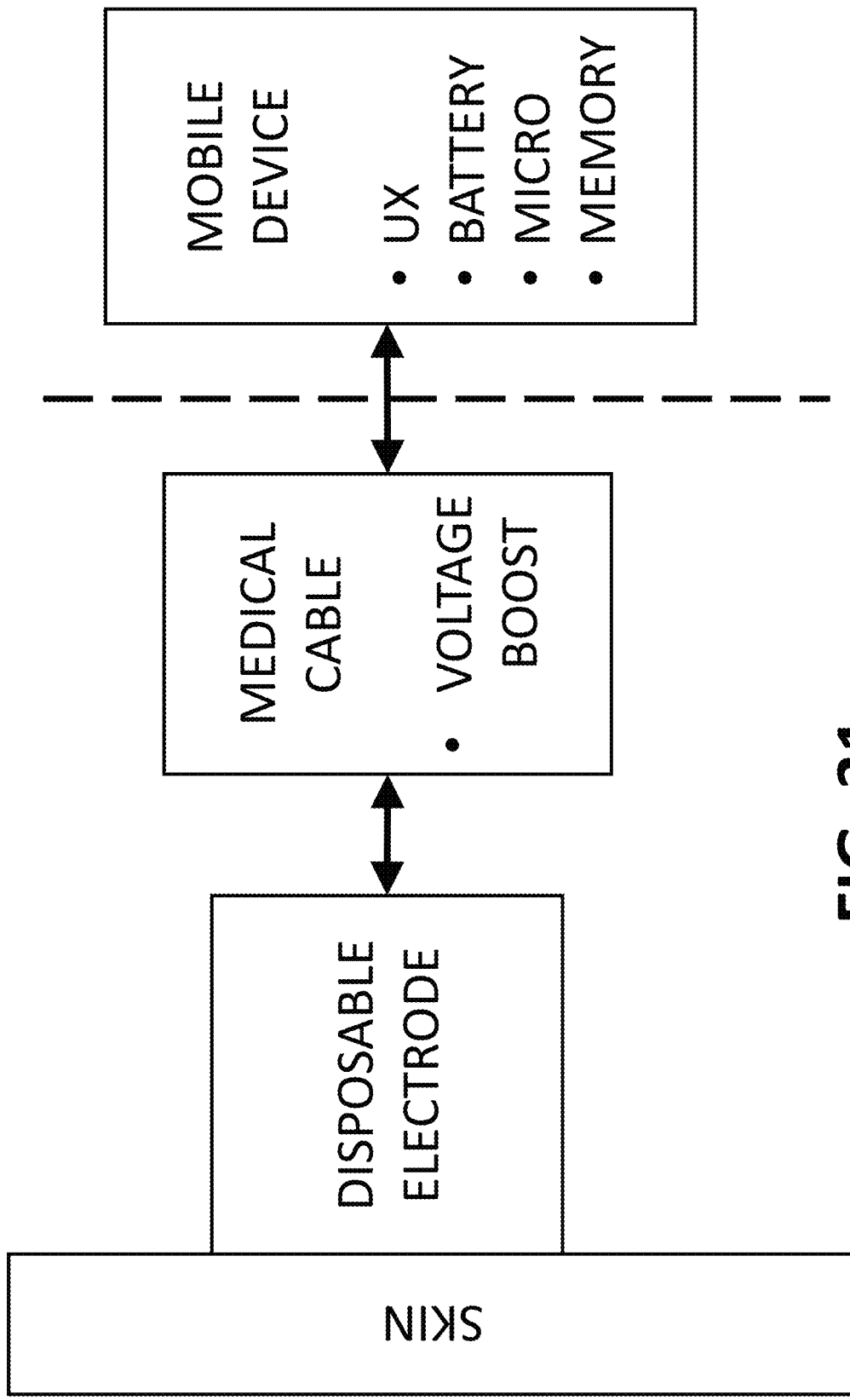
FIG. 31 is a block representation of general components within an electrical stimulation system disclosed herein.

FIG. 22 and FIG. 24 depict a system comprising electrode 101, medical cable 112 and stimulator/current generator 116. In this configuration, electrical elements including the battery, microprocessor, memory, and input/output interface (i.e. UX) are contained within housing 117. FIG. 31 represents an alternate system configuration in which the electrical component or components that serve to boost voltage (e.g. boost converter, transformer) from a nominal battery voltage (e.g. 3.7V, ≤12V) to a higher treatment voltage (e.g. 50V, 75V, 100V) are provided separate or separable from the other elements of the stimulator. In one embodiment a boost converter is contained within a medical cable and the other electrical elements are contained within a mobile device (e.g. smartphone, tablet computer). This configuration has the advantage of maximally utilizing existing capabilities of the mobile device and minimizing the number of application specific components (e.g. boost converter embedded in a medical cable, disposable electrode) required to deliver the therapeutic treatment. A variant of this system configuration comprises boost converter component separate from the medical cable and positioned between the medical cable and the mobile device. In another variant the boost converter is provided within the electrode.

Figure 32:
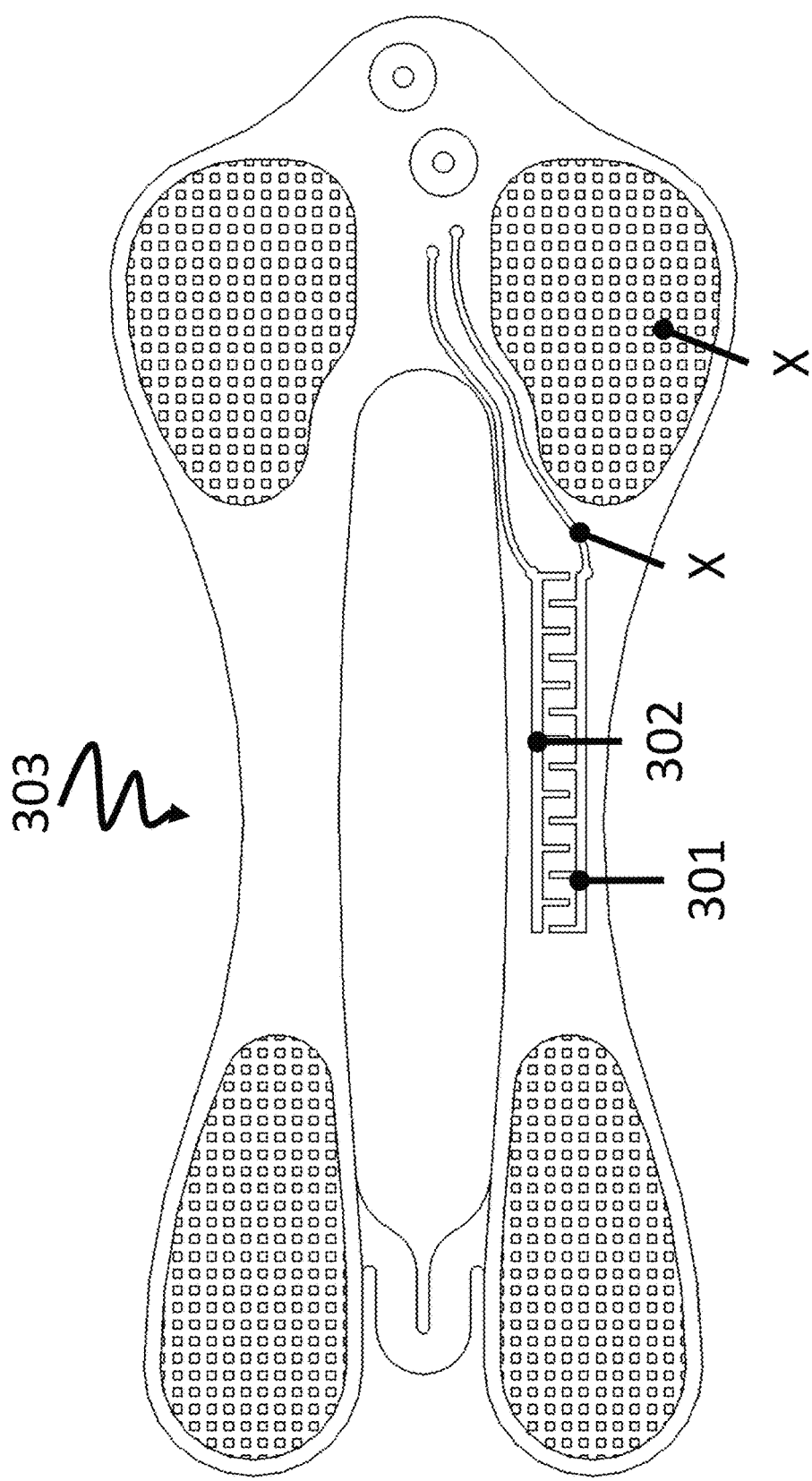
FIG. 32 shows a multi-layer printed circuit of an electrical stimulation device including moisture sensor.
Figure 33:
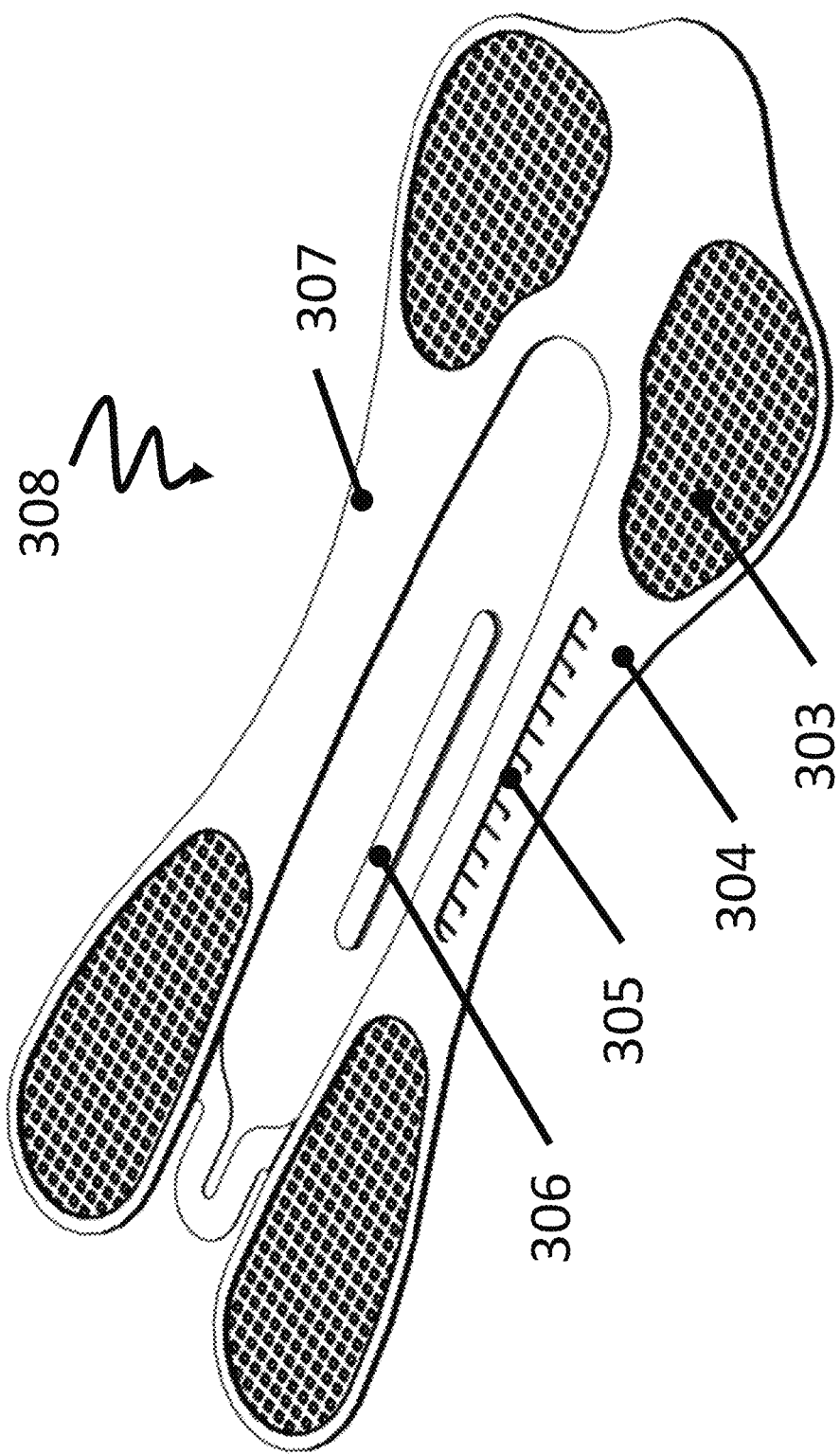
FIG. 33 shows the electrical stimulation device with moisture sensor of FIG. 32.

FIG. 32 depicts a subcomponent of another embodiment with similar characteristics to electrode 101 with a moisture sensor incorporated therein. Various moisture sensing techniques are known in the art. One technique utilizes first and second moisture sensor traces (301 and 302) on printed circuit 303 and spaced in closed proximity to one another. These first and second moisture traces may extend to a position where they are in proximity to studs (not shown, opposite side) that provide a connection point to a medical cable. The printed circuit 303 may comprise multiple alternating layers of conductive ink and non-conductive ink that permit the traces to overlay one another without being in electrical contact. FIG. 33 depicts the multi-layered printed circuit 303 underneath non-conductive layer 304 that exposes the four conductive regions and a portion of the moisture sensor 305. Non-conductive layer 304 can be fabricated from foam. The foam may be hydrophobic. A sensor overlay 306, shown as an exploded view, is fabricated from an absorbent material and positioned over moisture sensor 305. When the patient contacting surface 307 of electrode 308 (shown without conductive hydrogel) is wetted by the user sensor overlay 306 absorbs moisture and transfers it to moisture sensor 305. Now in contact with first and second moisture sensor traces (301 and 302), the moisture acts to reduce the electrical resistance between the traces, which is measured by the stimulator (not shown). The moisture sensor may alternatively be located proximate the anterior or tail end of the egress in closer proximity of the urethra opening.

Incorporation of a moisture sensor enables additional functionality. Upon sensing moisture the device may pause treatment as a safety measure. Further, the device may provide instruction to the user and log the event for future analysis. When the device is worn for multiple hours per day the moisture sensing data may provide insight regarding the severity of incontinence and any changes through time. After a therapeutic session, when the pelvic floor muscles are partly or fully fatigued, the patient may be more likely to experience a voiding event. Sensing these post-treatment voiding events provides information useful in determining whether the user is receiving too much or too little exercise during their treatment. Parameters (intensity, duration, duty cycle, etc.) for subsequent treatments can be modified accordingly. For example, if a patient is experiencing multiple voiding episodes in the 1 hour after treatment the device automatically increases the rest between contractions during subsequent treatments.

Figure 34:
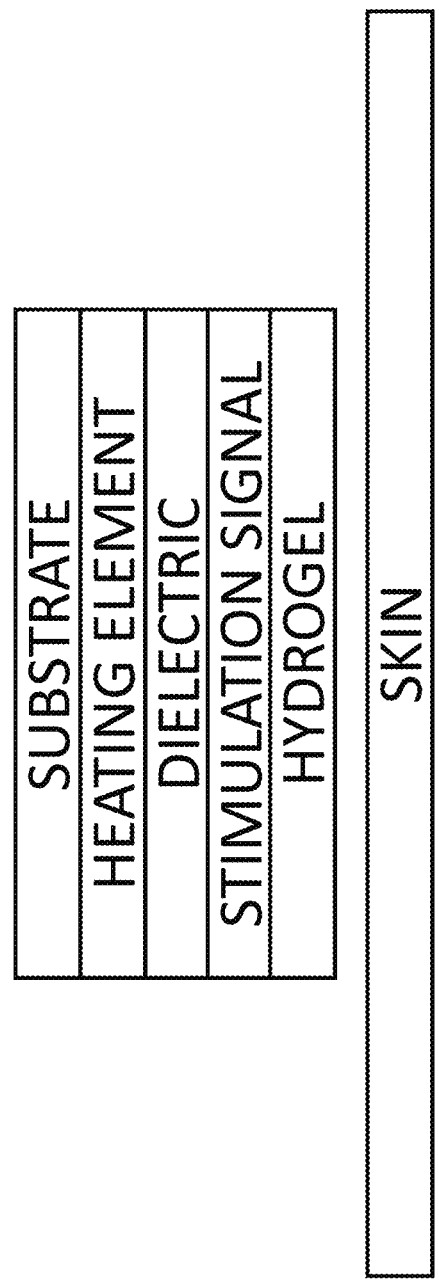
FIG. 34 is a block representation showing the layers of any embodiment of the disclosed electrical stimulation device with an added integrated heating element.
Figure 35:
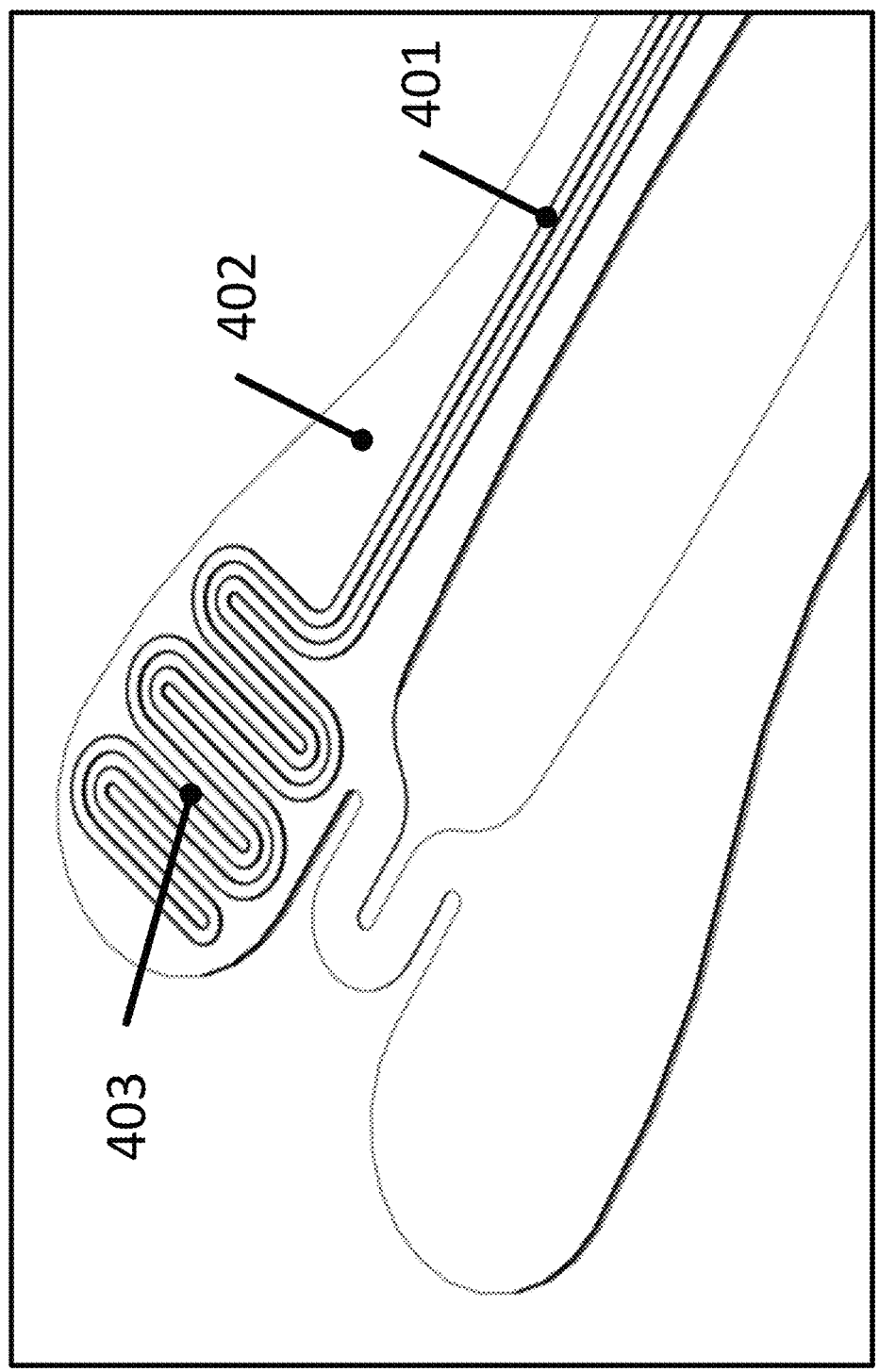
FIG. 35 is a partial perspective view of printed circuit of an electrical stimulation device with an integrated heating element.

Additional functionality can be integrated within the electrode in the form of a heating element. The heating element acts to warm the hydrogel prior to the user applying the electrode to skin. This is advantageous given that hydrogel, which has a high water content, is highly thermally conductive and perceived by some people to be uncomfortably cool when first applied. FIG. 34 is a representation of the layered construction of an electrode that includes a heating element. FIG. 35 shows an embodiment of a heating element on a layer within an electrode. An electrically conductive trace 401 is printed on a substrate 402 using a resistive ink that generates heat with the flow of electrical current. Trace 401 can be configured with multiple turnarounds 403, in which the path changes direction within a small region resulting in co-located tracings. In this embodiment turnarounds 403 are positioned proximate the hydrogel (not shown). While FIG. 35 only shows a single heating element 403, however, other embodiments exist with multiple heating elements, for example, a heating element like reference numeral 403 proximate each of the conductive regions in the electrode. To efficiently target delivery of heat to the conductive regions, certain embodiments may include tracings 401 fabricated with multiple ink chemistries. A first ink chemistry is used near turnarounds is resistive to generate heat and a less resistive second ink chemistry is used for tracing regions remote of the hydrogel. Alternatively, traces for both heating elements and conductive regions can be positioned in the same planar layer, typically in serpentine paths.

Figure 36:
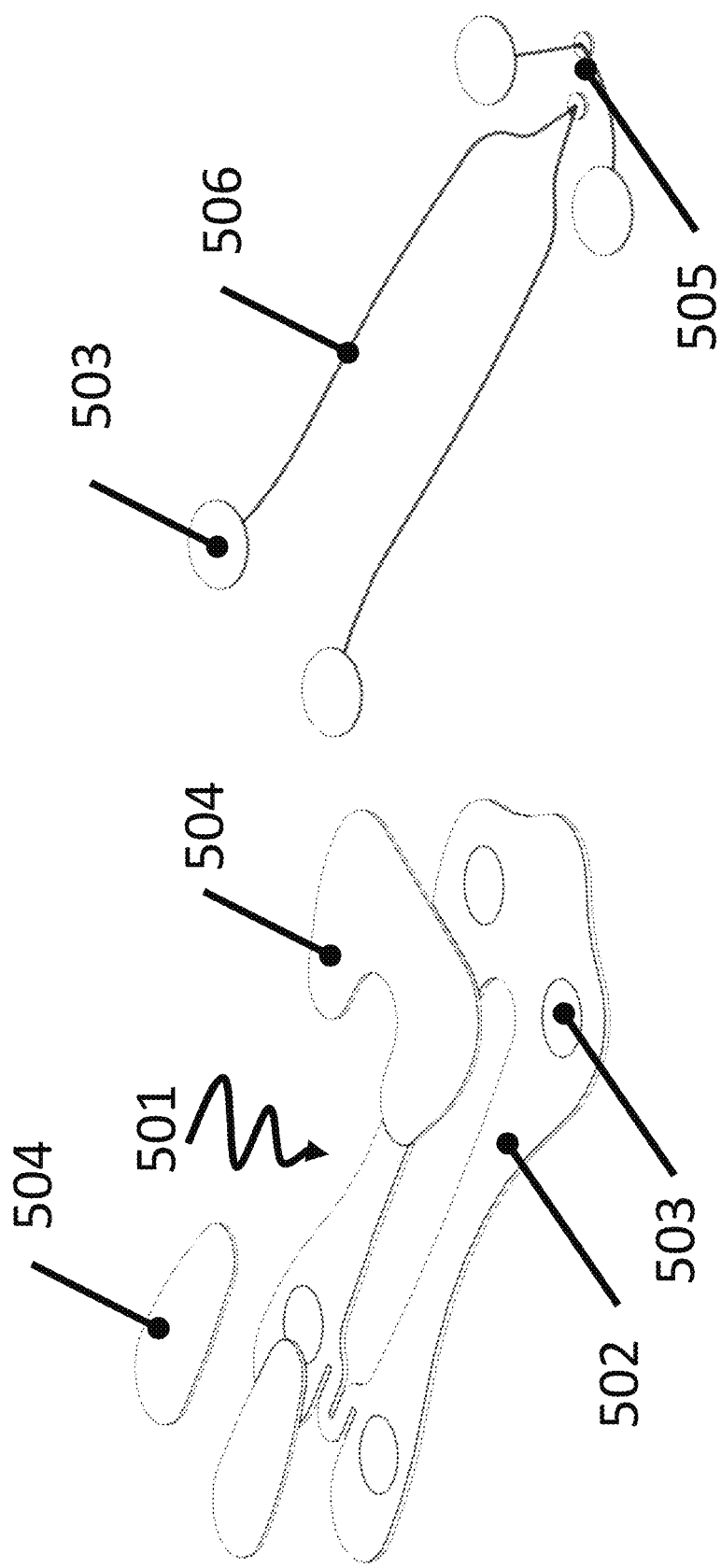
FIG. 36 show views of an electrical stimulation device according to the disclosure with partially reusable components.

FIG. 36 depicts the patient contacting side of an electrode 501 which is designed to be, in part, reusable. The electrode 501 comprises a body 502 of profile similar to electrode embodiments disclosed above. Embedded within body 502 are multiple conducting buttons 503 situated flush or proud of the patient contacting surface of body 502. Detachable electrically conductive hydrogel pads 504 are placed by the user such that the backsides of hydrogel pads 504 are in direct contact with conductor discs or elements 503. The discs 503 are in electrical connection with studs 505 that create a connection point to a current generating cable, like in previous embodiments (not shown in FIG. 36). The electrical connection between the discs 503 and studs 505 can be achieved with conventional wire 506, or either or both of the discs 503 and wiring 506 can be substituted with a printed circuit, as disclosed above. The local wiring 506 may be fully embedded within body 502 such that the body 502, conductors 503 and wiring 506 form a single integrated standalone electrode 501. The body feature of the electrode 501 can be formed by molding of polymers. Alternately, the body 502 can be fabricated from one or more layers of fabric. The hydrogel pads 504 may comprise a layer of carbon film or other conductive film suitable to uniformly distribute current density across an entire respective conductive region, which may be larger than the area of the conductive button 503. A portion of the button 503 and/or body 502 placed in contact with hydrogel pads 504 may include a surface finish or features that encourages adherence of hydrogel pads 504, making hydrogel pads 504 more likely to stick to electrode 501 than to skin.

Figure 37:
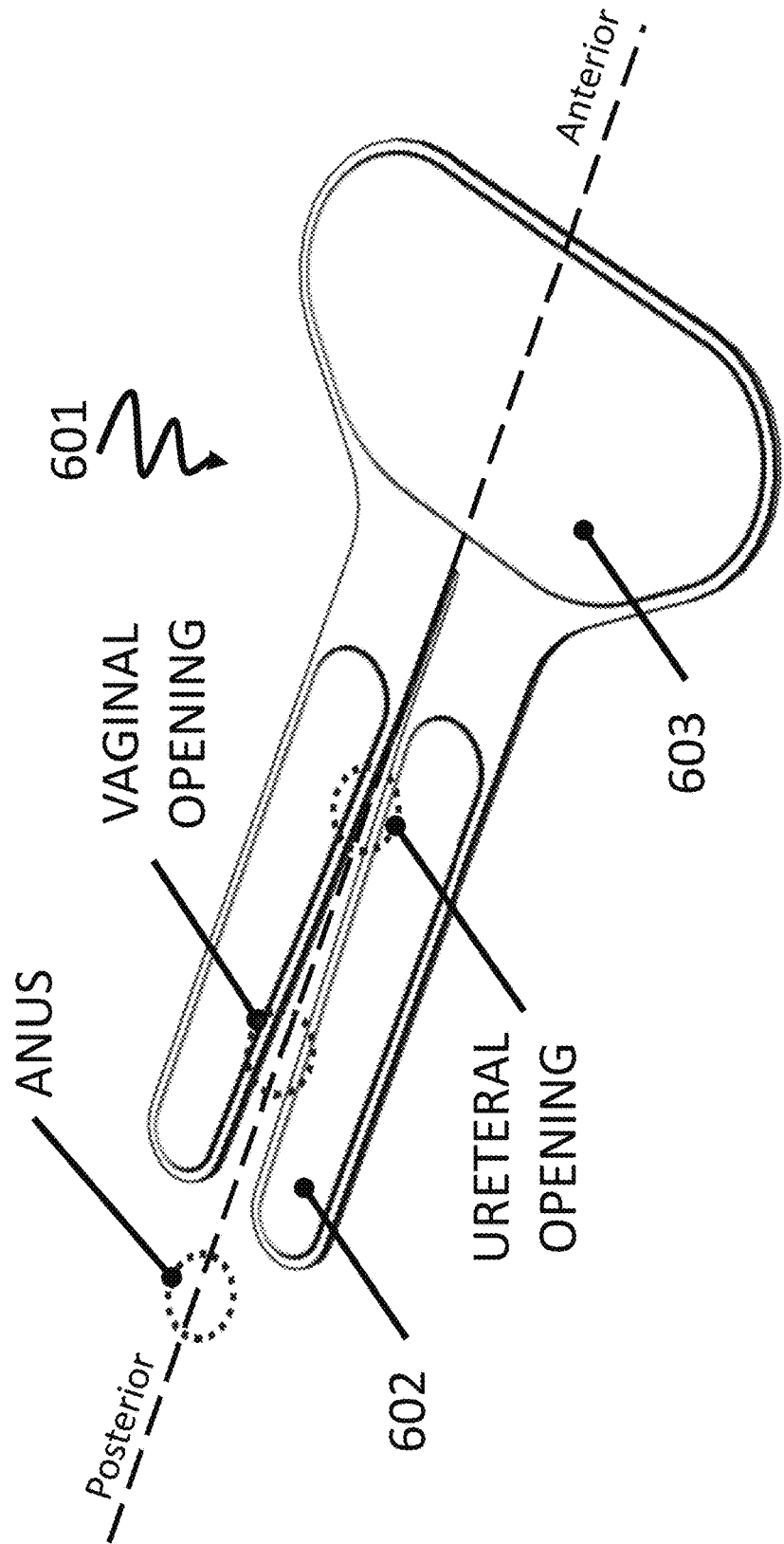
FIG. 37 shows another embodiment of an electrical stimulation device according to the disclosure.

FIG. 37 depicts another electrode 601, which is similar to the electrode shown as reference numeral 201 but with a relatively shorter length serving to position posterior conductive regions 602 substantially anterior to the anus. In this configuration the lateral width of each of the posterior conductive regions 602 on the tail portion is relatively narrower than posterior conductive regions 203 in electrode 201 and posterior conductive regions 102 in electrode 101. In certain embodiments, the anterior-posterior length of posterior conductive regions 602 is relatively increased to provide a conductive area similar to the conductive area of anterior conductive region 603 in the head portion of the body. Positioning of posterior conductive electrodes substantially anterior to the anus promotes targeted electrical stimulation of pelvic floor muscles most proximal to the ureter and reduces the degree of stimulation realized proximate the anus. In this configuration posterior conductive regions may be positioned on or proximate labial tissue on the individual being treated. In defining positioning of posterior conductive regions 602 as substantially anterior to the anus, the intent is that more than 50% of the surface area (e.g. >50%, >60%, >70%, >80%, >90%, 100%) can be positioned anterior to the anus.

Figure 38:
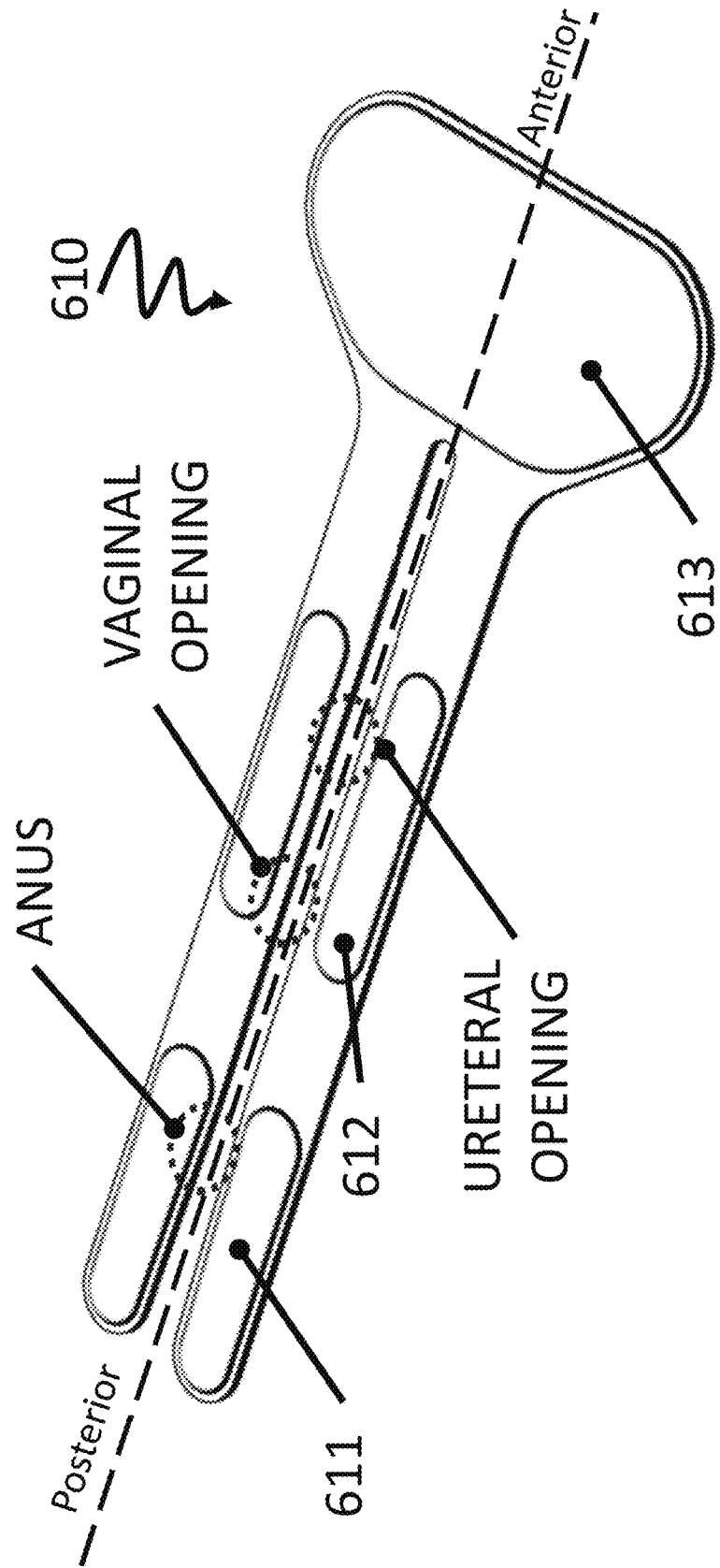
FIG. 38 shows an embodiment of an electrical stimulation device having posterior, intermediate and anterior conductive regions.
Figure 39:
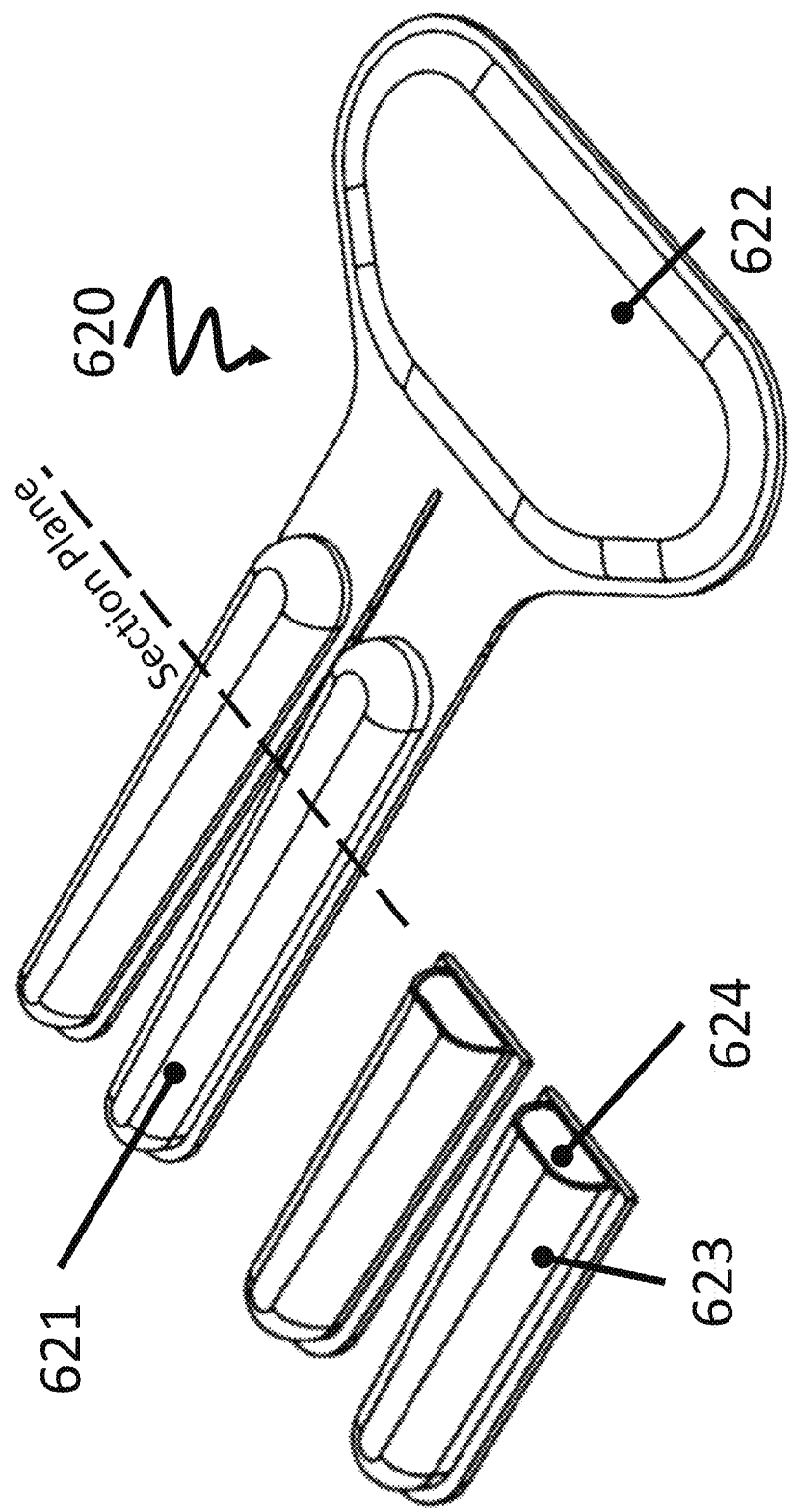
FIG. 39 is a perspective and section view of an electrical stimulation device with conductive regions having enhanced thickness.

FIG. 38 depicts an embodiment in which electrode 610 incorporates intermediate conductive regions 612 longitudinally between posterior conductive regions 611 and anterior conductive region 613. In typical use of the electrode 610, the intermediate conductive region 612 is positioned proximate the vaginal and ureteral openings in the individual with the posterior conductive region 611 positioned proximate the anus. Configured with three separately operable conductive regions (e.g. anterior, intermediate, posterior) a stimulator can deliver electrical muscle stimulation to target specific regions of the pelvic floor muscles.

By way of example, a first treatment or treatment portion delivers current between the anterior an intermediate conductive regions, then a second treatment or treatment portion delivers current between the intermediate and posterior conductive regions, then a third treatment or treatment portion delivers current between the anterior and posterior conductive regions. Stimulation of tissue between the anterior and intermediate regions relatively benefits the symptoms of stress incontinence. Stimulation of tissue between the intermediate and posterior regions relatively benefits the symptoms of urge incontinence by targeting the pudendal nerve. Stimulation of tissue between the anterior and posterior regions relatively benefits mixed incontinence. Various patterns of combining and cycling though these pairings are contemplated.

In another embodiment with design features similar to electrode 601, additional posterior conductive regions are presented on the opposing side of the electrode (i.e. not visible in FIG. 37). These additional posterior conductive regions contact the thigh tissue opposite labial tissue. In this way, the total area of device-patient contact is increased. In this configuration the two conductive regions on the left side are in electrical communication with one another. Similarly, the two conductive regions of the right side are in electrical communication with one another. This electrical communication can be achieve in a variety of ways including printing of electrically conductive traces on both sides of the substrate, through use of vias, and by wrapping the conductive elements (e.g. hydrogel and any underlying conductive materials) from one side to the other.

In another embodiment with design features similar to electrode 601, the electrode 620 includes electrically conductive resilient pads 623 positioned on each of the posterior conductive regions 621. Prior to use, electrode 620 is cooled or frozen. Then, when applied to the perineal tissue of users with vulvodynia, vulvar vestibulitis, or other pelvic pain associated conditions the cooling provides therapeutic benefit, including reduced pain, reduced inflammation, reduced swelling, local tissue numbing, disrupting pain reception, and increased circulation. Concurrently or following tissue cooling, electrode 620 delivers electrical stimulation therapy. The thickness of posterior conductive regions 621 (>1 mm, >3 mm, >5 mm, >10 mm, >15 mm) provides suitable heat capacity to achieve and maintain tissue cooling. Further, a large surface area of the conductive region 621 facilitates rapid heat transfer to all target tissues. In certain embodiments posterior conductive region 621 is comprised solely of hydrogel.

In other embodiments posterior conductive region 621 comprises a pouch or other closed volume 623 of electrically conductive material filled with electrically conductive filler 624 that has properties of a fluid or gel at room temperature. The composition of the gel material and in combination with the shape enables it to be malleable and conform to the body while in a cold/cool state. Posterior conductive region 621 may provide some measure of self-adherence to the skin. Alternately, the user may necessarily sit on electrode 620, which pushes posterior conductive region 621 against the symptomatic/injured tissue. Compliance of posterior conductive regions 621 allows them to take the shape of the tissue, providing more direct contact and heat transfer.

Therapy administered using the device may comprise delivery of a continuous or pulsed waveform for a defined period of time. The waveform may take a variety of forms known to be efficacious in TENS and electrical muscle stimulation therapy, including monophasic waveforms, biphasic waveforms, interferential currents, Russian type, etc. After the user sets an acceptable intensity level the device may modulate the intensity throughout the treatment (up or down) to achieve a desired therapeutic objective.

In one embodiment the device delivers different waveforms at times within the treatment session. By way of non-limiting example, during a first portion of the therapy the device delivers a waveform suitable to numb the local tissue (e.g. 1-8 minutes at 1-10 kHz). During a second portion of the therapy the device delivers a waveform suitable to contract the pelvic floor muscles (e.g. 1-30 minutes at 10-500 Hz). Because the tissue has been partially numbed, a higher intensity muscle contraction may be achieved with relatively less patient discomfort than if the treatment had consisted solely of the waveform suitable to contract the pelvic floor muscles. This approach may result in a greater therapeutic benefit. Other embodiments could comprise more than two portions within the treatment. By way of non-limiting example, treatment could alternate between numbing waveforms and contracting waveforms at prescribed intervals, between calming nerve waveforms and contracting muscle waveforms, or progress from one waveform to another to increase contraction intensity over time.

Specific preferred configurations and/or properties are applicable to all embodiments of the disclosed electrical stimulation device, including those identified as reference numerals 1, 101, 140, 201, 210, 303, 308. For example, the longitudinal spacing between anterior conductors and posterior conductors (D1), measured edge-to-edge, is approximately 30-150 mm, or more preferably approximately 60-100 mm, or even more preferably approximately 80-90 mm. A particular preferred embodiment includes anterior conductors spaced longitudinally approximately 84 mm apart from posterior conductors (edge-to-edge).

Additionally, the lateral spacing between respective posterior conductors, measured edge-to-edge (D2), is approximately 5-50 mm, or more preferably approximately 10-30 mm, and even more preferably approximately 20-25 mm. A particular preferred embodiment includes posterior conductors spaced laterally approximately 22 mm apart from each other (edge-to-edge). In the embodiments of the disclosed electrical stimulation device that include more than one spaced anterior conductor (see reference numerals 1, 101, 140, 303, 308) the preferred lateral spacing between them (D2') can be approximately the same as described above with respect to posterior conductors. Many of the disclosed electrical stimulation devices feature a D2 that is substantially equal to D2', although there is no requirement for the spacing D2 between respective posterior conductors to be equal to the spacing D2' between respective anterior conductors within the same device. Of course it is noteworthy that at least in the embodiments that include an expandable section or sections (see reference numerals 101, 140, 210, 303, 308) these specific distances are adjustable by the user.

Further, particular ratios of edge-to-edge longitudinal distance between anterior and posterior conductors to edge-to-edge lateral distance between respective posterior conductors or respective anterior conductors have been shown to deliver treatment benefits to users. Preferably, a ratio (D1:D2) between an edge-to-edge longitudinal distance D1 between the anterior conductor and the at least two posterior conductors, and an edge-to-edge lateral distance D2 between respective posterior conductors is within the range of approximately 1.5:1 to approximately 5:1, more preferably within the range of approximately 3:1 to approximately 5:1, and even more preferably within the range of approximately 3.5:1 to approximately 4.5:1, or approximately 2:1 to approximately 3:1. For example, embodiments exist with D1 of approximately 50 mm and D2 of approximately 25 mm; D1 of approximately 75 mm and D2 of approximately 25 mm; and D1 of approximately 80 mm and D2 of approximately 20 mm.

Features of the embodiments disclosed herein allow multi-hour wear. This affords the individual the convenience in receiving multiple treatment sessions in a day without needing to remove and re-apply the device multiple times per day. In one embodiment of the device, scheduling of these multiple treatments per day is partially automated by the device. The user determines when to initiate treatment or identifies that the device has been applied, and the device subsequently determines when each treatment will begin. The number of treatments per day may be specified by the user or by the device. The number of treatments per day may also change throughout a multi-week therapy regimen. By way of non-limiting example, two treatment sessions may be administered each day during the first time period (e.g. 1 week, 2 weeks), then three treatment sessions are administered each day during a second time period, and four treatment session during a third time period. The duration of each treatment session may also change throughout the multi-week therapy regimen. In different embodiments this adaptive therapy may informed by time (i.e. days, total treatment time), patient input, physician input, biofeedback, and known treatment algorithms. The treatments may be pre-programmed and based on actual usage of the device.

Described above with respect to the preferred embodiments of the electrical stimulation device is a characteristic of lateral symmetry, and in some cases longitudinal symmetry. Not only is the disclosed electrical stimulation device substantially symmetrical spatially and geometrically, but current flow through the respective conductors is also preferably substantially symmetrical. That is, the posterior conductors cooperate to pass substantially equal current as the anterior conductor or conductors. Similarly, the spaced posterior conductors work in tandem to pass a substantially balanced current across the longitudinal midline. The anterior conductor or conductors are also configured to pass a substantially equal current on each side of the longitudinal midline. In the embodiments that include a single anterior conductor, this symmetrical current flow is being achieved via an evenly distributed charge through the entire anterior conductor that is laterally spaced evenly about the longitudinal midline.

While a preferred embodiment has been set forth for purposes of illustration, the foregoing description should not be deemed a limitation of the invention herein. Accordingly, various modifications, adaptations and alternatives may occur to one skilled in the art without departing from the spirit of the invention and scope of the claimed coverage.

What is claimed is:

1. An electrical stimulation device for treating an individual or animal, comprising:
   a body made from an electrically insulating material with a head portion that transitions longitudinally to a tail portion;
   at least one activatable anterior conductor positioned on the head portion of the body;
   at least two activatable posterior conductors positioned on the tail portion of the body;
   wherein the electrical stimulation device is configured to be worn by the individual or animal, and
   the body has a lateral width defined between a left edge and a right edge which extend the longitudinal length of the body from the head portion to the tail portion, the body transitions inwardly longitudinally between the head portion and tail portion such that the lateral width at an intermediate portion is smaller than the lateral width of the tail or head portion, including a longitudinally extending void space in the body laterally between the left and right edge and longitudinally between the head portion and tail portion, the void space splitting the tail portion into a left side and a right side, the at least one activatable anterior conductor and at least two activatable posterior conductors cooperating to pass an electrical charge between one another to treat an area on the individual or animal on which the conductors are placed in contact.

2. The electrical stimulation device of claim 1, wherein the positioning of one of the at least two posterior conductors relative to another of the at least two posterior conductors is laterally movable.

3. The electrical stimulation device of claim 2, wherein the at least two posterior conductors are laterally spaced from one another with an expandable non-conductive section of the body therebetween.

4. The electrical stimulation device of claim 3, wherein the expandable non-conductive section of the body comprises a plurality of openings that allow deformation of the expandable non-conductive section to reciprocate the at least two posterior conductors relative to one another.

5. The electrical stimulation device of claim 3, wherein the expandable non-conductive section of the body limits the extent of lateral reciprocation between the at least two posterior conductors.

6. The electrical stimulation device of claim 1, comprising an expandable non-conductive section of the body positioned longitudinally between the anterior conductor and at least two posterior conductors, the expandable non-conductive section allowing longitudinal reciprocation of the at least two posterior conductors relative to the anterior conductor.

7. The electrical stimulation device of claim 1, wherein the body transitions in a direction toward the posterior end in a substantially V-shaped section.

8. The electrical stimulation device of claim 7, wherein one of the at least two posterior conductors is positioned on each side of the V-shaped section of the body.

9. The electrical stimulation device of claim 1, wherein a ratio D1:D2 between an edge-to-edge longitudinal distance D1 between the anterior conductor and the at least two posterior conductors, and an edge-to-edge lateral distance D2 between the respective posterior conductors is within the range of approximately 1.5:1 to approximately 5:1.

10. The electrical stimulation device of claim 1, wherein an edge-to-edge longitudinal distance D1 between the anterior conductor and the at least two posterior conductors is within the range of approximately 30 mm to approximately 150 mm.

11. The electrical stimulation device of claim 1, wherein an edge-to-edge lateral distance D2 between the respective posterior conductors is within the range of approximately 5 mm to approximately 50 mm.

12. The electrical stimulation device of claim 1, comprising at least two electrically conductive snapping member positioned on the body and configured for releasable mechanical and electrical attachment with a current generator for generating a charge through the respective conductors when the at least one snapping member is attached to the current generator and the generator is activated, wherein a first snapping member being electrically connected to each of the at least two posterior conductors and a second snapping member being electrically connected to the at least one anterior conductor.

13. The electrical stimulation device of claim 1, comprising two anterior conductors and two posterior conductors.

14. The electrical stimulation device of claim 13, wherein the body defines a longitudinally extending central opening between the anterior conductors and the posterior conductors.

15. The electrical stimulation device of claim 14, wherein a sagittal plane extends longitudinally from the head portion and tail portion between the left edge and right edge, and each of the anterior conductors is positioned on an opposite side of the sagittal plane.

16. The electrical stimulation device of claim 1, wherein each of the conductors is at least partially covered by an electrically conductive gel pad that is detachable from the electrical stimulation device.

17. The electrical stimulation device of claim 1, comprising local electrically conductive tracings extending between the conductors and a current generator for electrically connecting the conductors to the current generator, wherein the conductors and local electrically conductive tracings are molded into the body, the conductors, local electrically conductive tracings and body collectively forming a single standalone unit.

18. The electrical stimulation device of claim 1, comprising two posterior conductors, wherein a sagittal plane extends longitudinally from the head portion and tail portion between the left edge and right edge, and one posterior conductor is disposed on each side of the sagittal plane.

19. The electrical stimulation device of claim 1, wherein a total exposed area A1 of the least one anterior conductor is approximately equal to a total exposed area A2 of the at least two posterior conductors.

20. The electrical stimulation device of claim 1, wherein the total electrical current that is passed through the at least one posterior conductor on the right side is approximately equal to the total electrical current that is generated through the at least one posterior conductor on the left side when activated.

21. An electrical stimulation device for treating an individual or animal, comprising:
　　a body having a contact side and a non-contact side, extending longitudinally between an anterior end and a posterior end, and extending laterally between a left edge and right edge with a sagittal plane extending longitudinally therebetween;
　　at least one anterior activatable conductor positioned proximate the anterior end on the contact side of the body;
　　at least two posterior conductors positioned proximate the posterior end on the contact side of the body, at least one of the at least two posterior conductors being positioned on each side of the sagittal plane, wherein the electrical stimulation device is configured to be worn by the individual or animal, and
　　a spacing extends in the body in a direction toward the posterior end from an intermediate position located between the anterior end and posterior end, thereby splitting a portion of the body into a left side and a right side, with at least one of the posterior conductors being positioned each of the left side and the right side with a portion of the spacing disposed therebetween, and the contact side defines a surface configured for interfacing with perineal region in the individual or animal, whereby electrical current generated through the conductors when activated penetrates into the perineal region of the individual or animal.

22. The electrical stimulation device of claim 21, wherein the electrical current passed through the conductors when activated is substantially the same on each side of the sagittal plane.

23. The electrical stimulation device of claim 21, comprising one anterior conductor, wherein the sagittal plane passes through the anterior conductor such that a portion of the anterior conductor lies on one side of the sagittal plane and a portion of the anterior conductor lies on the other side of the sagittal plane.

24. The electrical stimulation device of claim 23, comprising two posterior conductors.

25. The electrical stimulation device of claim 21, comprising two anterior conductors, wherein the sagittal plane passes between the two anterior conductors such that one anterior conductor lies on one side of the sagittal plane and the other anterior conductor lies on the other side of the sagittal plane.

* * * * *